US010557148B2

(12) United States Patent
Aldwinckle et al.

(10) Patent No.: US 10,557,148 B2
(45) Date of Patent: Feb. 11, 2020

(54) COMPOSITIONS AND METHODS FOR DETERRING FEEDING BY PSYLLIDS

(71) Applicant: Cornell University, Ithaca, NY (US)

(72) Inventors: Herb Aldwinckle, Geneva, NY (US); Kerik Cox, Geneva, NY (US); Charles Linn, Farmington, NY (US); Ewa Borejsza-Wysocka, Geneva, NY (US); Jean-Michel Hily, Geneva, NY (US); Dong H. Cha, Geneva, NY (US)

(73) Assignee: Cornell University, Ithaca, NY (US)

( * ) Notice: Subject to any disclaimer, the term of this patent is extended or adjusted under 35 U.S.C. 154(b) by 4 days.

(21) Appl. No.: 15/315,743

(22) PCT Filed: Jun. 4, 2015

(86) PCT No.: PCT/US2015/034191
§ 371 (c)(1),
(2) Date: Dec. 2, 2016

(87) PCT Pub. No.: WO2015/187944
PCT Pub. Date: Dec. 10, 2015

(65) Prior Publication Data
US 2017/0191077 A1 Jul. 6, 2017

Related U.S. Application Data

(60) Provisional application No. 62/008,934, filed on Jun. 6, 2014.

(51) Int. Cl.
*C12N 15/82* (2006.01)
(52) U.S. Cl.
CPC .................. *C12N 15/8286* (2013.01)
(58) Field of Classification Search
None
See application file for complete search history.

(56) References Cited

U.S. PATENT DOCUMENTS

| | | | | |
|---|---|---|---|---|
| 5,824,861 | A * | 10/1998 | Aldwinckle | A01H 1/04 800/279 |
| 7,371,848 | B2 * | 5/2008 | Conner | C12N 15/8216 536/24.1 |
| 2006/0253925 | A1 | 11/2006 | Rupar et al. | |
| 2007/0248735 | A1 | 10/2007 | Keithly et al. | |
| 2009/0172838 | A1 | 7/2009 | Axtell et al. | |
| 2009/0229006 | A1 | 9/2009 | Jepson et al. | |
| 2010/0077506 | A1 | 3/2010 | Wiig et al. | |
| 2011/0244056 | A1 | 10/2011 | Santra | |
| 2013/0125254 | A1 * | 5/2013 | Dawson | C12N 15/8203 800/278 |
| 2013/0152227 | A1 * | 6/2013 | Chern | C07K 14/415 800/279 |
| 2014/0109472 | A1 | 4/2014 | Mirkov et al. | |

FOREIGN PATENT DOCUMENTS

EP 2 202 311 A2 * 3/2010

OTHER PUBLICATIONS

Malnoy et al., MPNI 20(12):1568-80 (2007).*
Ko et al., Food Chem 123:484-88 (2010).*
Halpin, Plant Biotech J 3:141-55 (2005).*
Hu et al., Biochem J 453:261-70 (2013).*
de Souza et al., Glycobiol 13(12):961-72 (2003).*
Herrero-Galán et al., Biochimie 94:427-33 (2012).*
Cao et al., Cell 88:57-63 (1997).*
Guo et al., Proc Natl Acad Sci USA 101:9205-10 (2004).*
Dutta et al., Plant Biotech J (3):601-11 (2005).*
Singer et al., Plant Mol Biol 74(3):293-305 (2010).*
GenBank Version No. U86836.1, "Hirsutella thompsonii hirsutellin A mRNA, complete cds." Dated Jan. 15, 2003 (1 page).
Boucias et al., "Cloning and sequencing of cDNA of the insecticidal toxin hirsutellin A," J Invertebr Pathol. 72:258-261 (1998).
Butler et al., "The potato psyllid, *Bactericera cockerelli* (Sulc) (Hemiptera: Triozidae): life history, relationship to plant diseases, and management strategies," Terrestrial Arthropod Reviews. 5:87-111 (2012).
Curtis et al., "A peroxidase gene promoter induced by phytopathogens and methyl jasmonate in transgenic plants," Mol Plant Microbe Interact. 10(3):326-338 (1997).
Garris, "Researchers put the squeeze on citrus disease by developing trees that taste bad to bugs," Cornell Chronicle, dated Jan. 16, 2012 (2 pages).
Hajdukiewicz et al., "The small, versatile pPZP family of Agrobacterium binary vectors for plant transformation," Plant Mol Biol. 25:989-994 (1994).
Herrero-Galán et al., "The insecticidal protein hirsutellin A from the mite fungal pathogen *Hirsutella thompsonii* is a ribotoxin," Proteins 72(1):217-28 (2008).
Kay et al., "Duplication of CaMV 35S Promoter Sequences Creates a Strong Enhancer for Plant Genes," Science. 236(4806):1299-1302 (1987).
Orbovic et al., Chapter 17: Citrus. *Agrobacterium Protocols, Second Edition*, vol. 2. Kan Wang (Ed.). Totowa, New Jersey: Humana Press, 177-189 (2006) (16 pages).
Singer et al., "The sucrose synthase-1 promoter from Citrus sinensis directs expression of the beta-glucuronidase reporter gene in phloem tissue and in response to wounding in transgenic plants," Planta. 234:623-637 (2011).
van Engelen et al., "pBINPLUS: an improved plant transformation vector based on pBIN19," Transgenic Res. 4:288-290 (1995).
International Search Report for International Patent Application No. PCT/US15/34191, dated Nov. 23, 2015 (6 pages).

(Continued)

*Primary Examiner* — Russell T Boggs
(74) *Attorney, Agent, or Firm* — Clark & Elbing LLP

(57) ABSTRACT

The invention relates to a plant that includes a transgene encoding a heterologous polypeptide conferring on plant expressing said polypeptide resistance to a hemipteroid sap-sucking insect. The transgene is also expressed in a plant component (such as a leaf). Typically, expression of such polypeptides deters feeding by insects such as psyllids (such as an Asian citrus psyllid, the African citrus psyllid, or the American citrus psyllid). Exemplary plants useful in the invention are citrus or solanaceous plants.

15 Claims, No Drawings

Specification includes a Sequence Listing.

(56) References Cited

OTHER PUBLICATIONS

Written Opinion of the International Searching Authority for International Patent Application No. PCT/US15/34191, dated Nov. 23, 2015 (10 pages).
International Preliminary Report on Patentability for International Patent Application No. PCT/US15/34191, dated Dec. 6, 2016 (11 pages).
Search Report for Spanish Patent Application No. 201690065 dated Aug. 28, 2017 (4 pages) (No English language translation provided).

* cited by examiner

COMPOSITIONS AND METHODS FOR DETERRING FEEDING BY PSYLLIDS

CROSS-REFERENCE TO RELATED APPLICATIONS

This application claims benefit of U.S. Provisional Application No. 62/008,934, filed Jun. 6, 2014, which is hereby incorporated by reference in its entirety.

FIELD OF THE INVENTION

The present invention generally relates to the field of plants expressing insect inhibitory proteins. In particular, the present invention relates to proteins exhibiting insect inhibitory activity against agriculturally relevant pests of crop plants such as solanaceous and citrus plants particularly hemipteroid sap-sucking insect pests such as the Asian citrus psyllid, the African citrus psyllid, the American citrus psyllid, and the potato/tomato psyllid, Bactericera cockerelli.

BACKGROUND OF THE INVENTION

Psyllids are small phloem feeding insects that typically feed on either a single plant, or a few related plants. They can serve as vectors for different microbial species that can act as plant pests. They are also suspected of delivering toxins to plant species as they feed, causing pathogenesis.

The citrus psyllids from Asia, Africa, and America are small insect pests that feed on the leaves and stems of citrus trees. These psyllids transmit a bacterial disease called Huanglongbing (HLB), also known as citrus greening disease. All citrus and closely-related species are susceptible hosts for both citrus psyllid insects and HLB disease. This bacterial disease is transmitted to healthy trees by the psyllid after it feeds on infected plant tissue. Once a citrus tree is infected with HLB, there is no cure and the plant will eventually die. The best way presently to prevent the disease from killing citrus trees is to stop these citrus psyllids.

The potato/tomato psyllid, Bactericera cockerelli, has been a longstanding pest of solanaceous crops, including potatoes, tomatoes, peppers, and eggplants. It can damage plants through direct feeding, is suspected of delivering a plant toxin, and also transmits the bacterial pathogens Liberibacter psyllaurous and Liberibacter solanacearum. In potatoes, it is thought to cause a systemic disease called psyllid yellows that includes a reduction in growth, yellowing of leaves, erectness of new foliage, leaf abnormalities, shortened and thickened internodes, enlarged nodes, aerial tubers, premature senescence and early plant death. In tomatoes, the foliage symptoms are similar to that of potatoes, and fruit set, size, texture, and yield can be decreased. B. cockerelli and the transmission of L. solanacearum has also been linked to zebra chip disease in potatoes, which causes stunting, chlorosis, swollen internodes of the upper growth, proliferation of axillary buds, aerial tubers, browning of the vascular system, leaf scorching, and premature plant death. Different insecticides have been used against B. cockerelli, however, recently some resistance to common treatments has been detected in psyllid populations in California (Butler and Trumble, Terrestrial Arthropod Reviews, 5, 87-111, 2012).

No control method is currently available that will eliminate psyllids and the risk of pathogen transmission within a citrus grove or field of solanaceous crops. Methods to suppress psyllid infestation will likely slow the spread of the disease and maintain the economic feasibility of crop production.

It is in view of these issues that the invention described herein was developed.

SUMMARY OF THE INVENTION

We have discovered that several genes from the Hirsutella fungus that colonizes insects and from Allium (the onion family) and other genes described herein are useful, when expressed in transgenic plants, for inhibiting feeding by psyllid insects. Accordingly, the invention provides purified nucleic acid molecules, vectors (such as expression vectors), cells, plants and plant components, products, and methods useful for protecting plants from diseases, for example, citrus greening, and zebra chip disease caused by psyllids.

In one aspect, the invention features a plant including a transgene encoding a heterologous polypeptide, the polypeptide conferring, on a plant expressing the polypeptide, resistance (as is described herein) to a hemipteroid sap-sucking insect pest. In preferred embodiments, the insect is a psyllid such as the Asian citrus psyllid. In other preferred embodiments, the plant is resistant to infestation by psyllids. In yet other preferred embodiments, the plant is resistant to feeding by psyllids. The invention accordingly features plants that are non-attractive to sap-sucking insects. In particularly preferred embodiments, the plant is a citrus plant. Exemplary plants accordingly include any member of the rue family including, but not limited to, orange, lemon, lime, and grapefruit plants. Preferably, the transgene is operably linked to regulatory sequences (such as heterologous regulatory sequences) for expression of the polypeptide, and wherein the regulatory sequences include a promoter (e.g., a constitutive promoter or a cell-specific promoter such as a promoter active in phloem cells or phloem tissue of a plant). Exemplary polypeptides are substantially identical to HtA (native), HtA (short), ASAL (native), ASALR (native), ASALR (short), ACA (native), ACA (short), ACT (native), or ACT (short), MpNPR1 or CsNPR1 as are described herein. In other preferred embodiments, polynucleotides encoding the polypeptides are stacked according to conventional techniques (as is described herein). Combinations of one or more polynucleotides in a transgenic plant or plant component are also contemplated. Plants expressing such polynucleotides typically evidence increased yield compared to a control plant.

In another aspect, the invention features a product derived from a transgenic plant expressing any polynucleotide described herein, wherein the product includes a detectable amount of the transgene or a polypeptide expressed from the polynucleotide. Preferably, the product is a citrus product, or a solanaceous plant product.

In yet another aspect, the invention features a progeny plant or seed, wherein the progeny plant or seed includes a transgene expressing one or more of the polynucleotides described herein. In some embodiments, the progeny plant or seed includes an herbicide resistance gene conferring resistance to the herbicide.

In another aspect, the invention features a polynucleotide having substantial identity to HtA (native), HtA (short), ASAL (native), ASALR (native), ASALR (short), ACA (native), ACA (short), ACT (native), or ACT (short), MpNPR1 or CsNPR1 (each is described herein), optionally wherein the polynucleotide is operably linked to regulatory sequences for expression of the polypeptide, and wherein the regulatory sequences include a promoter.

In another aspect, the invention features an expression construct that includes a polynucleotide that expresses one or more polypeptides conferring on a plant resistance to a hemipteroid sap-sucking insect. Exemplary polynucleotides are those having substantial identity to HtA (native), HtA (short), ASAL (native), ASALR (native), ASALR (short), ACA (native), ACA (short), ACT (native), ACT (short), MpNPR1, or CsNPR1. In other preferred embodiments, the polynucleotide is complementary to at least 20 contiguous nucleotides of a sequence selected from the group of HtA (native), HtA (short), ASAL (native), ASALR (native), ASALR (short), ACA (native), ACA (short), ACT (native), ACT (short), MpNPR1, or CsNPR1. In other preferred embodiments, the polynucleotide is operably linked to a heterologous regulatory sequence such as a CaMV 35S promoter, a CaMV 35S tandem promoter, Shpx6b promoter, a SUS1 promoter, or a CsSUS1 promoter. In still other preferred embodiments, the polynucleotide is operably linked to a nos-terminator. In yet other preferred embodiments, the polynucleotide is expressed in phloem tissue of a plant.

In another aspect, the invention features a plant cell, a plant, or plant component including one or more of the polynucleotides or expression constructs described herein. In particular, the invention features plants that are members of the Citrus genus such as *Citrus sinensis, Citrus sinensis* L. Osbeck 'Hamlin', or *Citrus sinensis* L. Osbeck 'Valencia'.

In still another aspect, the invention features propagating any of the transgenic plants (such as citrus and potato) as is described herein by vegetative propagation.

In still another aspect, the invention features a product derived from the plant cell, plant, or plant component which includes one or more of the polynucleotides described herein, wherein the product includes a detectable amount of the recombinant polynucleotide. In preferred embodiments, the product is a citrus product or a solanaceous product, which may include, but is not limited to, citrus fruit, citrus fruit juice, and citrus fruit juice concentrate.

In other aspects, the invention features a method of controlling a hemipteroid sap-sucking insect, the method including exposing the insect to the plant cell, plant, or plant component that includes one or more of the polynucleotides described herein, wherein the plant cell, plant, or plant component expresses a polypeptide that inhibits feeding, e.g., directly or indirectly, by the insect. In general, the method, for example, involves rendering a plant less attractive to feeding or infestation by psyllids.

In another preferred aspect, the invention features a method of making a plant resistant to citrus greening, the method including the steps of introducing into a plant cell one or more of the polynucleotides described herein; and regenerating from the plant cell a transgenic plant expressing an insect inhibitory amount of a polypeptide encoded by the polynucleotide; and, optionally, demonstrating Asian citrus psyllid resistance as a property of the transgenic citrus plant or the transgenic citrus plant component. Again the method, in general, involves making a plant less attractive for feeding or infestation by psyllids.

In yet another preferred aspect, the invention features a method of making a plant resistant to zebra chip disease and psyllid yellows, the method including the steps of introducing into a plant cell one or more of the polynucleotides described herein; and regenerating from the plant cell a transgenic plant expressing an insect inhibitory amount of a polypeptide encoded by the polynucleotide; and, optionally, demonstrating *B. cockerelli* resistance as a property of the transgenic solanaceous plant or the transgenic solanaceous plant component.

In another aspect, the invention features a method for obtaining citrus juice, the method, in general, involves providing fruit harvested from a plant expressing a polypeptide that confers resistance to a hemipteroid sap-sucking insect pest and extracting citrus juice from the plant such as a fruit provided from such plant. In preferred embodiments, juice is extracted from a fruit of a citrus plant such as an orange, lemon, lime, or grapefruit. In other preferred embodiments, the method further involves concentrating the citrus juice. In still other preferred embodiments, the method further involves fortifying the citrus juice (e.g., vitamins and nutrients thiamin and potassium, vitamin D and calcium). Additionally, if desired, the method further involves fortifying the citrus juice concentrate.

In yet other aspects, the invention features a method of obtaining citrus fruit such as oranges, lemons, limes, and grapefruit, the method involving harvesting fruit from a plant expressing a polypeptide that confers resistance to a hemipteroid sap-sucking insect.

By "nucleic acid molecule" or "polynucleotide" is meant a molecule, e.g., RNA or DNA, having a sequence of two or more covalently bonded, naturally occurring or modified nucleotides. The nucleic acid molecule may be, e.g., single or double stranded, and may include modified or unmodified nucleotides, or mixtures or combinations thereof. Various salts, mixed salts, and free acid forms are also included.

By "nucleic acid fragment" or "polynucleotide fragment" is meant a contiguous segment of a nucleic acid molecule. The length of a nucleic acid segment can range from at least one base pair (e.g., at least 10, 20, 30, 40, 50, 60, 70, 80, 90, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, or 450 base pairs) up to the full length of the nucleic acid molecule. When a nucleic acid molecule is herein referred to as having more than one nucleic acid fragment, it is understood that these nucleic acid fragments may occupy non-overlapping portions of the nucleic acid molecule.

By "sequence identity" is meant (in the context of comparing the sequence of a nucleic acid molecule or a nucleic acid fragment to a reference sequence or comparing the amino acid sequence of a polypeptide to a reference sequence) that the nucleic acid molecule or nucleic acid fragment has the same sequence as the reference sequence or has a specified percentage of nucleotides that are the same at the corresponding locations within the reference sequence when the full length sequence of the nucleic acid molecule or nucleic acid fragment is optimally aligned with the full length of the reference sequence. Within this context, the percentage of nucleotides that are the same between two sequences is computed with reference to the length of the longer sequence. Sequence identity can be computed between DNA and DNA, RNA and RNA, or DNA and RNA. When a sequence identity is computed between DNA and RNA, it is well-appreciated in the art that thymidine residues are equivalent to uracil residues for purposes of this calculation. Furthermore, it is well-appreciated in the art that if the percent sequence identity of the reverse complement sequence to the reference sequence is greater than that of the forward sequence, then the percent sequence identity is the former quantity. The Needleman-Wunsch algorithm, for example, may be used to determine sequence identity based on optimal global alignments. Sequence identity can be computed between polypeptides as well according to standard methods. Computer programs for determining nucleic acid sequence identity or polypeptide identity (e.g., protein blast) are publicly available at, for example, the European Bioinformatics Institute (EMBL-EBI) website or using BLAST® found at the National Library of Medicine website.

By "substantially identical" is meant (in the context of comparing the sequence of a nucleic acid molecule or a nucleic acid fragment to a reference sequence or comparing the amino acid sequence of a polypeptide to a reference sequence) that the sequences have a sequence identity, as calculated using methods described above, of at least 85% (e.g., at least 85%, 87%, 90%, 92%, 95%, 96%, 97%, 98%, 99%, or even 100%).

By "resistance to a plant pest" is meant a level of resistance to a pest (e.g., a hemipteroid sap-sucking insect such as a psyllid such as the Asian citrus psyllid) in a transgenic plant (or plant component or cell) greater than the level of resistance relative to a control plant (e.g., a non-transgenic plant). In one embodiment, the level of resistance to a pest in a transgenic plant is at least 5 to 10% (and preferably 20%, 30%, or 40%) greater than the resistance of a control plant. In other embodiments, the level of resistance to the pest is 50% greater, 60% greater, and more preferably even 75% or 90% greater than a control plant; with up to 100% resistance as compared to a control plant being most preferred. The level of resistance is measured using conventional methods. For example, the level of resistance to a psyllid is assayed by comparing non-attractiveness of a transgenic leaf to the psyllid versus a control leaf. In another example, the level of resistance to psyllid infestation is assayed. And in still another example, the level of resistance to psyllid feeding is assayed in transgenic plants versus control plants as a measure of determining effectiveness of expression of a heterologous polypeptide to confer resistance to the plant as is described herein.

By "operably linked" is meant that a gene and a regulatory sequence(s) are connected in such a way to permit gene expression when the appropriate molecules (e.g., transcriptional activator proteins) are bound to the regulatory sequence(s).

By "polypeptide" or "protein" is meant any chain of amino acids, regardless of length or post-translational modification (for example, glycosylation or phosphorylation).

By "plant cell" is meant any self-propagating cell bounded by a semi-permeable membrane and containing a plastid. Such a cell also requires a cell wall if further propagation is desired. Plant cell, as used herein includes, without limitation, any cell obtained from seeds, suspension cultures, embryos, meristematic regions, callus tissue, leaves, roots, shoots, pollen, and microspores.

By "plant component" is meant a part, segment, cutting, liquids, fibers, or an organ obtained from an intact plant. Exemplary plant components include, without limitation, seeds, somatic embryos, bark, leaves, stems, pollen, roots, shoots, flowers, tendrils, fruits, scions, and rootstocks, juices, and juice concentrates as well as any plant part used for vegetative propagation.

By "transgene" is meant any piece of a nucleic acid molecule (e.g., DNA) which is inserted by artifice into a cell, and becomes part of the genome of the organism which develops from that cell. Such a transgene may include a gene which is partly or entirely heterologous (i.e., foreign) to the transgenic organism, or may represent a gene having sequence identity to an endogenous gene of the organism.

By "transgenic" is meant any cell which includes an isolated nucleic acid molecule (e.g., a DNA sequence) which is inserted by artifice into a cell and becomes part of the genome of the organism which develops from that cell. As used herein, the transgenic organisms are generally transgenic plants and the DNA (for example, a transgene) is inserted by artifice into the nuclear or plastidic genome. A transgenic plant may contain one or more of the isolated nucleic acid molecules described herein.

As discussed herein, several polynucleotides have been identified, isolated or engineered, and characterized which are useful in providing resistance against psyllids. Accordingly, the invention provides a number of important advances and advantages for the protection of plants against pests. For example, the invention facilitates an effective and economical means for in-plant protection against plant pests by deterring insect pest feeding. Such protection against pests reduces or minimizes the need for traditional chemical practices (for example, application of bactericides or insecticides or both) that are typically used by farmers for controlling the spread of plant pests and providing protection against disease-causing pests such as the Asian citrus psyllid and the potato/tomato psyllid. In addition, because plants with one or more of the polynucleotides described herein are less vulnerable to pests and their diseases, the invention further provides for increased production efficiency, as well as for improvements in quality and yield of an agricultural crop plant such as citrus crop plants and solanaceous plants. Thus, the invention contributes to the production of high quality and high yield citrus-based agricultural products, for example, fruits, juices, as well as crops having reduced spots, blemishes, and blotches that are caused by pests including reduced greening due to HLB; agricultural products with increased shelf-life and reduced handling costs; and high quality and yield crops for agricultural, industrial, and commercial purposes. Furthermore, because the invention reduces the necessity for chemical protection against plant pests, the invention benefits the environment where the crops are grown.

DETAILED DESCRIPTION

This application describes making transgenic plants or transgenic plant components having psyllid pest resistance; in particular, in, for example, deterring feeding or infestation by psyllids on transgenic citrus plants or plant components such as, but not limited to, 'Hamlin' or 'Valenicia' sweet oranges, tomato, and potato.

Insect Pest Inhibitory Polynucleotides and Polypeptides

Polynucleotides substantially identical to the following sequences are useful for generating transgenic plants having resistance to hemipteroid sap-sucking insects (such as to render a plant or plant component non-attractive to, for example, psyllids). Synthetic polynucleotide sequences may be designed so that they will be expressed in plants. A variety of standard methods for synthesizing plant genes to improve the expression level of the protein encoded by the synthesized gene are known in the art. Such methods, in general, relate to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of expressed polypeptide.

1. *Hirsutellin* A ("HtA"): a ribotoxin gene from the fungus, *Hirsutella*
   a. "Native"

(SEQ ID NO: 1)
ATGAAGGCCTTTACTGCCATTCTCGCCAGCGCGGCCTTGTTCGCCACCGG
CCTCGCGGCTCCCGCCTCAGAAGCCACCTCGGTGAACAGCCTGGAAGAGC
GCGCTCCCATCGTCACCTGCCGGCCCAAGCTCGACGGGCGGGAGAAGCCG
TTCAAGGTAGACGTGGCGACGGCGCAGGCACAGGCGCGCAAGGCGGGCCT
GACGACGGGCAAGAGCGGCGACCCTCACCGGTACTTCGCCGGCGACCACA
TCCGCTGGGGCGTCAACAACTGCGACAAGGCGGACGCGATCCTGTGGGAG
TACCCGATCTACTGGGTCGGCAAGAACGCCGAGTGGGCCAAGGACGTCAA
GACGTCGCAGCAAAGGGAGGGCCGACGCCGATCCGCGTCGTCTACGCCA
ACAGCAGGGCGCCGTGCAGTACTGCGGCGTCATGACGCACAGCAAGGTC
GACAAGAATAACCAGGGCAAGGAGTTCTTTGAGAAGTGCGATTAG b. Polypeptide:

(SEQ ID NO: 2)
Met K A F T A I L A S A A L F A T G L A A P A S E
A T S V N S L E E R A P I V T C R P K L D G R E K
P F K V D V A T A Q A Q A R K A G L T T G K S G D
P H R Y F A G D H I R W G V N N C D K A D A I L W
E Y P I Y W V G K N A E W A K D V K T S Q Q K G G
P T P I R V V Y A N S R G A V Q Y C G V Met T H S
K V D K N N Q G K E F F E K C D c. "Short"

(SEQ ID NO: 3)
ATGGCTCCCATCGTCACCTGCCGGCCCAAGCTCGACGGGCGGGAGAAGCC
GTTCAAGGTAGACGTGGCGACGGCGCAGGCACAGGCGCGCAAGGCGGGCC
TGACGACGGGCAAGAGCGGCGACCCTCACCGGTACTTCGCCGGCGACCAC
ATCCGCTGGGGCGTCAACAACTGCGACAAGGCGGACGCGATCCTGTGGGA
GTACCCGATCTACTGGGTCGGCAAGAACGCCGAGTGGGCCAAGGACGTCA
AGACGTCGCAGCAAAGGGAGGGCCGACGCCGATCCGCGTCGTCTACGCC
AACAGCAGGGCGCCGTGCAGTACTGCGGCGTCATGACGCACAGCAAGGT
CGACAAGAATAACCAGGGCAAGGAGTTCTTTGAGAAGTGCGATTAG d. Polypeptide:

(SEQ ID NO: 4)
Met A P I V T C R P K L D G R E K P F K V D V A T
A Q A Q A R K A G L T T G K S G D P H R Y F A G D
H I R W G V N N C D K A D A I L W E Y P I Y W V G
K N A E W A K D V K T S Q Q K G G P T P I R V V Y
A N S R G A V Q Y C G V Met T H S K V D K N N Q G
K E F F E K C D

2. ASAL: A Lectin Gene from *Allium ampeloprasum*
   a. Native:

(SEQ ID NO: 5)
ATGAGCGTGGCCACTGTAGCCACCATCCTAACCATTTTGGCATCTACATG
CATGGCCAGAAACGTATTGGTGAACAACGAAGGACTGTACGCAGGCCAAT
CCCTAGTCGAGGAACAGTACACTTTTATAATGCAGGATGACTGCAACCTT
GTACTGTATGAATACAGCACCCCCATCTGGGCCTCAAACACAGGCATCAC
CGGTAAAAATGGGTGCAGGGCCGTGATGCAGCCTGATGGCAACTTTGTCG
TCTACGATGTTAAGGGGCGTGCCGTCTGGGCCAGTAACAGCAGAAGAGGG
AACGGGAACTATATCCTGGTGCTTCAGAAGGACAGAAACGTTGTTATTTA
CGGATCTGATATTTGGTCTACTGGCACATACCGGAAAAAAGTGGGTGGAA
CTGTTGTTATGGCTATGAGTGGTACGGTCGATGGAGGCTCCGCGATTGGA
CCGGTAACAGTGAATCAGAATGTCACTGCCGTCCGAAAGGTTGCAGCAGC
TGCTGCTGCTTGA b. Polypeptide:

(SEQ ID NO: 6)
Met S V A T V A T I L T I L A S T C Met A R N V L
V N N E G L Y A G Q S L V E E Q Y T F I Met Q D D
C N L V L Y E Y S T P I W A S N T G I T G K N G C
R A V Met Q P D G N F V V Y D V K G R A V W A S N
S R R G N G N Y I L V L Q K D R N V V I Y G S D I
W S T G T Y R K K V G G T V V Met A Met S G T V D
G G S A I G P V T V N Q N V T A V R K V A A A A
A

6. MpNPR1: A Regulatory Gene Involved in Basal Plant Resistance in Apple
   a. Nucleotide Sequence:

(SEQ ID NO: 19)
ATGGCTCATTCAGCCGAACCATCATCCTCTCTGAGCTTTACTTCATCACC
CCATTTATCAAATGGTTCAATAAGCCACAACTTATCGTGTTCTGGCTCCG
AATCGGTGCCAAGTCTTGAAGTCATCAGTTTGTCCAAGCTTAGCTCTAGT
TTGGAGCAGTTGTTGATTGATCCTGGCTGTGACTATAGTGATGCTGATAT
CGTAGTTGAGGGGATTCCTGTTGGTGTACACCGATGTATATTGGCTTCTA
GGAGTGGATTTTTTCGCGAGCTATTCAAGCGAGAAAAGGGGTCTTCTGGA
AAGGAAGACAGGCCAAAGTACTGTATGAGTGATTTTCTGCCTTATGGCGA
TGTTGGATATGAAGCCTTCTTGGTTTTCTTAAGCTATGTGTATACTGGAA
AGCTTAAGCCTTCTCCCGTGGAGGTGTCAACCTGCGTTCACAATGTATGT
GCCCATGACGCATGTAGACCTGCTATCAATTTCGTTGTGGAATTGATGTA
CGCCGCTTCCATTTTCCAAATGCCCGATCTGGTTTCGATATTCGAGCGGC
GCCTTCTTAATTTTGTTGGGAAAGCTCTGTCAGACAATGTTGTCCCAATT
CTCTTGGTTGCCTTCCATTGTCAGTTGAATCAGCTCATCGATCAGTGTGT
AGATAGAGTGGCACGATCAGATATTGATGACATCTCTCTTGAGAAGGGAC

-continued

TTCCTGATGAGGTTGTGAAGAAAATCAAAATTCTTCGCCGCAATTATCAG

CAGGATTCTGACCCAAACTTGCCACCTGCCGATCCCTTGCATGAAAAGAG

AATCCGAAGAATACATAAGGCTTTGGACTCGGATGATGTCGAGCTTGTGA

AACTTCTTTTAACGGAGTCTAATATAACCTTAGATGAAGCCAATGCTCTC

CATTATGCTGCAGCTTACTGCGATCCTAAGGTTGTGACCGAAGTGCTTGC

TCTGGGCCTCGCTGATGTTAACCTCCGGAATTCTAGGGGTTATACAGTGC

TTCACATTGCTGTGATGCGCAAAGAGCCATCAATTATTGTATTGCTACTG

ACTAAAGGAGCTCGTGCATCGGAGCTGACATCAGATGGTCAGAGTGCTGT

TAGTATTTGCAGGAGGTTGACGAGACCAAAGGATTACCATTCAAAAACAG

AGCAGGGGCAAGAAGCAAACAAAGACCGAATATGCATCGATGTTCTAGAG

AGGGAAATGCGGCGGAATCCAATGGCTGGAGATGCATCTATATCTTCCCA

AATAATGCCCGATGATCTGCACATGGAGTTGCTGAACCTGGAGAACAGAG

TGGCATTGGCCCGATTGTTTTTCCCTGCGGAAGCCAAGCTAGCCATGGTC

ATTGCCCATGCGGAGACATCTGAGTTTGCTGCGCCATCATCATCGAAAGG

ATCAAGTGGGAATCTGATGGAGGTAGATTTAAACGAGACCCCCACCGTGC

AGAACAAAAGACTTCATTCCAGGTTGGAAGCCCTTATGAAAACAGTCCGT

TTGGGTAGATGCTACTTCCCTCATTGCTCAGAAGTCCTGGATAAGTTCAT

CGATGACGACCTCCCTCATTTGTTTTACCTCGAGCCTGGCTCCTCCGACG

AGCAGAAGGTAAAGAGGAGGCGTTTCATGGAGCTCAAGGAGGAAGTACAA

AAAGCATTTGACAAGGACAAGGCCGAGTGTAACCTCTCCGGATTGTCTTC

ATCGTCCTCCACGACATCTCCGGAAAAAATTGGTGCAAATCAGAAGGTTA

GGGAACCGTGA b. Polypeptide Sequence:

(SEQ ID NO: 20)
MetAHSAEPSSSLSFTSSPHLSNGSISHNLSCSGSESVPSLEVISLSKLS

SSLEQLLIDPGCDYSDADIVVEGIPVGVHRCILASRSGFFRELFKREKGS

SGKEDRPKYCMSDFLPYGDVGYEAFLVFLSYVYTGKLKPSPVEVSTCVHN

VCAHDACRPAINFVVELMYAASIFQMPDLVSIFERRLLNFVGKALSDNVV

PILLVAFHCQLNQLIDQCVDRVARSDIDDISLEKGLPDEVVKKIKILRRN

YQQDSDPNLPPADPLHEKRIRRIHKALDSDDVELVKLLLTESNITLDEAN

ALHYAAAYCDPKVVTEVLALGLADVNLRNSRGYTVLHIAVMRKEPSIIVL

LLTKGARASELTSDGQSAVSICRRLTRPKDYHSKTEQGQEANKDRICIDV

LEREMRRNPMAGDASISSQIMPDDLHMELLNLENRVALARLFFPAEAKLA

MVIAHAETSEFAAPSSSKGSSGNLMEVDLNETPTVQNKRLHSRLEALMKT

VRLGRCYFPHCSEVLDKFIDDDLPHLFYLEPGSSDEQKVKRRRFMELKEE

VQKAFDKDKAECNLSGLSSSSSTTSPEKIGANQKVREP

7. CsNPR1: A Regulatory Gene Involved in Basal Plant Resistance in Citrus

Useful CsNPR1 sequences are isolated and identified according to standard methods. For example, genomic DNA is extracted from *C. sinensis* cv. *valencia* (Four Winds Growers, Winters, Calif.) using an E.Z.N.A. Plant DNA extraction kit according to the manufacturer's instructions (Omega Bio-Tek, Norcross, Ga.). Since no CsNPR1 sequence had been previously published from *C. sinensis*, a genomic region including a 5' portion of the coding sequence is cloned initially using degenerate primers designed based on CLUSTAL alignments made with known MpNPR1 mRNA sequences from *Malus×domestica* (GenBank accession EU624123.1). An approximately 1800-bp fragment will be amplified from *C. sinensis* genomic DNA using primers CsNPR1degF1 (tggctgtgactatagtgatgct) (SEQ ID NO: 21) and CsNPR1degR1 (ccctaaccttctgatttgcacc) (SEQ ID NO: 22) at a 1 µM final concentration and GoTaq Hot Start Mastermix (Promega, Madison, Wis.). Cycling parameters will be 95° C. for 2 minutes, 35 cycles of 95° C. for 30s, 50° C. for 30s, 72° C. for 1 minute, and a final elongation of 72° C. for 5 minutes.

5' rapid amplification of genomic ends (RAGE) is then carried out according to Liu et al. (Plant Mol Biol Rep 19:261-267, 2001) to clone the region upstream of the CsNPR1 coding sequence. Briefly, genomic DNA is extracted from *C. sinensis* cv. *valencia* leaves using the OMEGA SP Plant DNA midi kit according to the manufacturer's instructions (Omega Bio-Tek) and PCRs are performed using primers initially designed to anneal near the 5' end of the CsNPR1 coding sequence. Progressively upstream 5' fragments are obtained using a gene-walking strategy. All PCR products are then cloned into a vector for sequencing such as pGEM-T easy (Promega).

Plant Expression Constructs

The construction of expression cassettes for use in plants such as solanaceous and citrus plants is well established. Expression cassettes are DNA constructs where various promoter, coding, and polyadenylation sequences are operably linked. In general, expression cassettes typically comprise a promoter that is operably linked to a sequence of interest which is operably linked to a polyadenylation or terminator region. In certain instances including, but not limited to, the expression of transgenes in a plant, it may also be useful to include an intron sequence. When an intron sequence is included, it is typically placed in the 5' untranslated leader region of the transgene. In certain instances, it may also be useful to incorporate specific 5' untranslated sequences in a transgene to enhance transcript stability or to promote efficient translation of the transcript.

A variety of promoters can be used in the practice of this invention. One broad class of useful promoters is referred to as "constitutive" promoters in that they are active in most plant organs throughout plant development. For example, the promoter can be a viral promoter such as a CaMV35S promoter. The CaMV35S promoters are active in a variety of transformed plant tissues and most plant organs (e.g., callus, leaf, seed and root). Enhanced or duplicate versions of the CaMV35S promoters are particularly useful as well. Other useful promoters are known in the art.

Promoters that are active in certain plant tissues (i.e., tissue specific promoters) can also be used to drive expression of insect inhibitory proteins disclosed herein. Since certain insect pests such as psyllids are sap-sucking insects that typically feed by inserting their proboscises into the vascular tissue of host plants, promoters that direct expression of insect inhibitory proteins or fragments thereof in the vascular tissue of the transgenic plants are particularly useful in the practice of this invention. Exemplary phloem-specific promoters include, without limitation, the peroxidase gene promoter Shpx6b. Other useful phloem-preferred promoters include those isolated from a sucrose synthase 1 (SUS1) gene such as maize, tobacco, citrus, tobacco, or sugarcane. An exemplary promoter region from plum (*Prunus domestica* L. cv. Improved French) is shown below.

(SEQ ID NO: 23)
<u>TCCAATGATTGCTCCCATTAGCT</u>AATCAAATTAATAGTACATTATAGTAT

GATAAGATTCAGCATATTCTTCAAACTATCCTCTCATCTTTTTTATTAT

AATGTGTGTACATAGTAATTAAAAACATTAATCCAAAACCCAAGTTGGAT

TACATTAAACCCGTGAACCCAATGGGCTAGAATTGTAGGGTTTCATAGGG

AACAACAACTGCAAAGTCTAAAAAGTAAGAGAAACTCTCGTGAAACGGGG

ATAGCATTTTTTGGTCTCCGGGGCAGTAACAACATGATACATAGGATAAC

TTTTCCGATACATATGACAACTTCTCCACATGTCATGTTGTTATTGGCCG

GGGATAGCAAAACAGTGCTATCCGCGGTATAGGTGAGTTTTTTTCCTAAA

AAGCGGCCAAAAGTCCGACTTCTGAATCATCACCCAACCAGCACCTTCGC

CGATTAGACCCATGCATGCCCCTCTTTCTCTGCACTTTCCCTGACCGCCA

CATATTTATTTTTTATTTCACACCTTAATTCCAT<u>GAATTTGGTGCCTTCA</u>

<u>ATGGG</u>AAAAAAAAAAAAAAAAAAAACCAGAAAATCCCAATGGATTTTTCTT

GTTGCCCAAGCCCGACAAAAAAAGGCAAATGCTTGAATATCAAGGCTTAA

AATTAAACAGCACAAAATTGATTAATCCTCTAATTTCTTTCCAAAAATCC

TATCATATCCCATTTTCAATTTGTGAATTTACGAAATTACCCCTGTTTTT

TTGATGACTTCTTCGGTCTTCGGGTAAGGAAATGAGACTGATAAAATGGA

TATAATAGATTTCCGACCACCCTGCTGGATTTTTTTTTGCCACTGCCCT

TATTATCGTACGCTCCAAGTTTTTTTTTACTTGCCTATTTTGGTTCGCG

GTTCCACGCTATAAAGCGAGCTCAC<u>ACCATCCACCAACCACCTCAC</u>TTCT

CTTCTTCTCGTTTCCATAGGCTTTCTCTCTCTCTGTGTTCTTTGTCTA

GGTACACCTCATTTTCTCTTCCCATTTTTATTTTTCCTTGTGTTCTTGTT

CTTCTTGTTGGGTTATTTCTTTAGGCTATATGGTCTTTGCTCTTTTTTC

TTTTGGTTCATCTCCCAAATCACATAGATCAATGCCTTCTGAATGTAGGG

TTGAGTTTATTTGAGGGTATATACTCTGTTTTTGCTTTTCTGCACCAGTA

TTTTGTGCGGATCTCTGTTTTTAATTTTTT<u>CCGTCTGCTTTTGTTTGTT</u>

<u>GAAAGTGAAAAAGCTGTTTATCTTTTTGACTGGTTGGTCTGTTTCA</u>

*CTTCAAC*

TTTTCAGCTTCTCTTTTGGAGAAAAGATTGATTCTTGTCAACATTCGCCA

AATGCACCATTTTTATTTTCTTCTTCTTTGATAAAAAGCGTTTTCTCTG

CTTTTGCTAAGCACCCTTAATTATTAATATTATAAGCCTGGATTTTTATG

ATGGGCTTGAAGCTTTTTATCTGTCCGCCACTCTGCAAATCCTTTATGGG

TGCATCTAATTATTACATAATTAAAACCTGGATCTTTTTTTCATTATTCT

TAACCACTATCTAAGGTTGCATCTTTGTTCAACCGCACTGCTCTAATTAA

CGTTTGTATGA*GGTGGTTGGTGG*ATGGTGTGTTTGGTTTTGAAAAACTAA

AGAAATTAGTCTTCTAGAATAATAAATAATATTAATAATAATAATATTAT

TATTATTGTAAAGTCTTCCTGTTAATGTTGGAATTATTGACTTGGTGGTG

ATTATCCATCTCTTTTTATTGCGAAGCTTCTGGATACCTTGTTATACTCA

-continued
CGGCTTGCTTTGTACTTGCAGTTTTTGAAG<u>GTTCTCTGATTTACCAATCT</u>

<u>GCTATCA</u>ATG

ATG (in bold) shows the start codon of the SUS1 gene. Underlined sequences correspond to primers used for downstream study to perform deletions constructs (at sequences of 1379, 978 and 672 nucleotides). Sequences in bold italics in SEQ ID NO:23 correspond to elements conferring xylem specificity in *Phaseolus vulgaris* described by website Plant Care (bioinformatics).

Still another useful phloem-specific promoter is the sucrose synthase-I promoter from *Citrus sinensis* (CsSUS1p) (Singer et al., *Planta* 234:623-637 (2011).)

Transcriptional enhancer elements can also be used in conjunction with any promoter that is active in a plant cell or with any basal promoter element that requires an enhancer for activity in a plant cell. Transcriptional enhancer elements can activate transcription in various plant cells and are usually 100-200 base pairs long. The enhancer elements can be obtained by chemical synthesis or by isolation from regulatory elements that include such elements, and can comprise additional flanking nucleotides that contain useful restriction enzyme sites to facilitate subsequence manipulation. Enhancer elements can be typically placed within the region 5' to the mRNA cap site associated with a promoter, but can also be located in regions that are 3' to the cap site (i.e., within a 5' untranslated region, an intron, or 3' to a polyadenylation site) to provide for increased levels of expression of operably linked genes. Such enhancers are well known in the art.

Additionally 5' untranslated leader sequences can be operably linked to a coding sequence of interest in a plant expression cassette. Thus the plant expression cassette can contain one or more 5' non-translated leader sequences which serve to increase expression of operably linked nucleic acid coding sequences encoding any of the polypeptides described herein.

Sequences encoding peptides that provide for the localization of any of the polypeptides described herein in subcellular organelles can be operably linked to the sequences that encode the particular polypeptide. Thus polypeptides that are operably linked to a signal peptide are expected to enter the secretion pathway and can be retained by organelles such as the endoplasmic reticulum or targeted to the vacuole by operably linking the appropriate retention or targeting peptides to the C-terminus of the polypeptide. Examples of vacuolar targeting peptides as well as peptides for targeting to plant plastids are well known in the art.

As noted above, the polynucleotide sequence of interest can also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' untranslated regions contain polyadenylate signals and represent non-limiting examples of such 3' untranslated regions that can be used in the practice of this invention. It is understood that this group of exemplary polyadenylation regions is non-limiting and that one skilled in the art could employ other polyadenylation regions that are not explicitly cited here.

Any of the aforementioned plant expression elements can be used with a polynucleotide designed to express one or more of the polypeptides encoded by any of the polynucleotides described herein (such as a polypeptide having substantial identity to HtA (native), HtA (short), ASAL (native), ASALR (native), ASALR (short), ACA (native), ACA (short), ACT (native), or ACT (short), MpNPR1 or CsNPR1) in a plant or a plant component. Plant expression cassettes including one or more of the polynucleotides described herein which encode one or more of their respective polypeptides, or insect inhibitory proteins encoding portions thereof that will provide for expression of one or more polypeptides in a plant are provided herein. A preferred plant expressible polynucleotide sequence can be evaluated for optimal expression in protoplast cells derived from the plant species of interest or a related plant species, or according to any of the methods described herein. After selection of those designed polynucleotide sequences which give the best expression, the selected sequences are then transformed into stable plants for continued selection.

The DNA constructs that include the plant expression cassettes described above are typically maintained in various vectors. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Selectable markers encoding genes that confer resistance to antibiotics are also typically included in the vectors to provide for their maintenance in bacterial hosts.

Transgenic Plants and Methods for Obtaining Insect Inhibitory Transgenic Plants

Methods of obtaining a transgenic plant (or a transgenic plant components) capable of inhibiting insect pests are also provided by this invention. First, expression vectors suitable for expression of any of the polypeptides disclosed herein plants are introduced into a plant, a plant cell or a plant tissue using transformation techniques according to standard methods well known in the art. Next a transgenic plant containing the plant expression vector is obtained by regenerating that transgenic plant from the plant, plant cell or plant tissue that received the expression vector. The final step is to obtain a transgenic plant that expresses an insect inhibitory amount of the polypeptide. Transgenic plants expressing insect inhibitory amounts of one or more polypeptides (such as substantial identity to HtA (native), HtA (short), ASAL (native), ASALR (native), ASALR (short), ACA (native), ACA (short), ACT (native), or ACT (short), MpNPR1 or CsNPR1 or any combination thereof) contemplated herein include, but not limited to, solanaceous plants such as tomato and potato and citrus plants such as oranges, lemons, limes, and grapefruit.

Plant expression vectors can be introduced into the chromosomes of a host plant via methods such as *Agrobacterium*-mediated transformation, particle-mediated transformation, DNA transfection, or DNA electroporation, or by so-called whiskers-mediated transformation. Exemplary methods of introducing transgenes are well known to those skilled in the art. For example, methods for production of transgenic Citrus via *Agrobacterium*-mediated transformation of juvenile or adult tissue are described in Orbović and Grosser, "Chapter 17: Citrus" in *Agrobacterium Protocols*, Second Edition, Volume 2, Kan Wang, editor, Humana Press, Totowa, N.J. (2006).

Those skilled in the art will further appreciate that any of these gene transfer techniques can be used to introduce the expression vector into the chromosome of a plant cell, a plant tissue, a plant, or a plant component.

After the plant expression vector is introduced into a plant cell or plant tissue, the transformed cells or tissues are typically regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants is well known in the art. This regeneration and growth process typically includes the steps of selection of transformed cells and culturing selected cells under conditions that will yield rooted plantlets. The resulting transgenic rooted shoots are thereafter planted in an appropriate plant growth medium such as soil. Transgenic plants having incorporated into their genome transgenic DNA segments encoding one or more of the polypeptides described herein are within the scope of the invention. It is further recognized that transgenic plants containing the DNA constructs described herein, and materials derived therefrom, may be identified through use of PCR or other methods that can specifically detect the sequences in the DNA constructs.

Once a transgenic plant is regenerated or recovered, a variety of methods can be used to identify or obtain a transgenic plant that expresses an inhibitory amount of one or more of the polypeptides described herein. One general set of methods is to perform assays that measure the amount of the polypeptide that is produced. Alternatively, the amount of mRNA produced by the transgenic plant can be determined to identify plants that express insect inhibitory amounts of the polypeptide.

Transgenic plants that express insect inhibitory amounts of the polypeptide can also be identified by directly assaying such plants for insect inhibition, for example, as described herein.

Sap-Sucking Insect Pest Control

Transgenic plants including polynucleotides encoding one or more of the polypeptides described herein or insect-inhibitory fragments thereof can be used in methods of controlling insect infestations.

Exemplary transgenic plants include, without limitation, citrus plants such as, but not limited to, 'Hamlin' or 'Valencia' sweet oranges (*Citrus sinensis* L.), and solanaceous plants such as the potato (*Solanum tuberosum* L.).

Transgenic citrus plants such as a transgenic orange plant (such as 'Hamlin' sweet orange) and the potato or tomato that are attacked by sap-sucking insect pests inhibited by one or more of the polypeptides described herein are useful in agriculture.

Preferred transgenic plants (or transgenic plant components) include polynucleotides encoding one or more polypeptides described herein or insect-inhibitory fragments thereof that are protected from sap-sucking insect feeding or infestation. Such transgenic plants are particularly effective for controlling species of hemipteroid sap-sucking insects such as psyllids that pierce and/or suck the fluids from the cells and tissues of plants.

Transgenic plants expressing insect inhibitory amounts of the insect inhibitory polypeptides or insect-inhibitory fragments thereof are first identified by any one of the methods described herein. Initial insect inhibition can be conducted in controlled environmental conditions (i.e., in enclosed growth chambers or greenhouses) evaluating insect (e.g., psyllid) feeding. Transgenic plants can also be subjected to insect infestation in field tests and compared against non-transgenic control plants. If desired, the non-transgenic control plants will include both plants treated with insecticides and untreated plants. Transgenic plant lines (i.e., transgenic plants derived from distinct transformation events including transgene insertions into different genomic locations) that display the insect inhibitory activity (such as rendering a plant less attractive to pysillid infestation or feeding) are selected for potential development for use in a variety of different genetic backgrounds (i.e., genetically distinct cultivars, varieties, and/or hybrid germplasms). Methods of introgressing transgenes into distinct germplasms and producing seed lots that primarily include transgenic seed are known to those skilled in the art. For example, the transgene can be fixed in a homozygous state in a desired genetic background. Once the transgene is fixed in that background, the homozygous transgenic plant can be used to produce transgenic seed of non-hybrid crops. Alternatively, the homozygous transgenic plant can be used as a pollen donor or recipient to produce transgenic seed of hybrid crops.

Specific types of transgenic plants expressing insect inhibitory polypeptides that inhibit specific insect pests are contemplated by this invention. Transgenic citrus plants such as, but not limited to, 'Hamlin' or 'Valencia' orange plants expressing insect inhibitory polypeptides that inhibit the Asian citrus psyllid are specifically contemplated.

EXAMPLES

The following examples are representative of the invention. The specific details disclosed herein are not to be construed as limiting.

Example 1—Plant Expression Constructs

Schematic representations of the transforming constructs described herein are shown in Tables 1 and 2. All vectors were produced using standard protocols and include pBINplus (van Engelen et al., Transgenic Res 4:288-290, 1995) with an inserted PZP-RSC1 multiple cloning site (Hajdukiewicz et al., Plant Mol Biol. 25:989-994, 1994) as a background, and were verified by sequencing prior to transformation. All constructs contained either a partially duplicated 35S promoter (referred herein to as 35S; Kay et al., Science 236:1299-1302, 1987), the peroxidase gene promoter Shpx6b of the legume *Stylosanthes humilis* (Curtis et al., MPMI 10: 326-338, 1997), the sucrose synthase 1 (SUS1) promoter from plum (*Prunus domestica* L. cv. Improved French) cloned as described herein, and the sucrose synthase-I promoter from *Citrus sinensis* (CsSUS1) (Singer et al., Planta 234: 623-637, 2011) fused to the nopaline synthase transcriptional terminator (nos-t). All promoter nos-t fusion cassettes were then inserted into the multiple cloning site in a pBINplus vector and cloned into the DH-5a strain of *Escherichia coli*, using the pGEMTeasy kit (Promega, Madison, USA) as per manufacturer's instructions.

Subsequently, cDNA's native and mature (short) versions of constructs were obtained by PCR amplification of cDNA preparations from tissues of *Hirsutella thompsonii, Malus× domestica, Allium cepa assagi* (ACA), *Al. roseum* (ASAL-ros) and *Al. ampeloprasum* (ASAL). Primers for amplification of the native and mature HtA cDNA sequences were obtained from Boucias et al., *J. of invert. Pathol* 72:258-261, 1998, but modified to contain BamHI and SacI restriction sites for ease of cloning, at the 5' and 3' end, respectively. Primers for amplification of the MpNPR1 cDNA were obtained mRNA sequences from *Malus×domestica* (GenBank accession EU624123.1), but modified to contain BamHI and SacI restriction sites for ease of cloning, at the 5' and 3' end, respectively. Primers for native and mature (short) *Allium* genes were also modified to contain BamHI and SacI restriction sites for ease of cloning, and were designed from known sequences (GenBank accession no. U58947 for ASAL and accession no. L12172 for ACA). These primers are as follows:

```
ASAL native: F primer
                                        (SEQ ID NO: 24)
5'-GGCGGATCCATGGGTCCTACTACTTCATCTCCT-3', ASAL native: R primer
                                        (SEQ ID NO: 25)
5'-GGCGAGCTCTCAAGCAGCACCGGTGCCAACCTT-3', ACA native: F primer
                                        (SEQ ID NO: 26)
5'-GGCGGATCCATGGAGAAACGTATTGGTGAACAA-3', ACA native: R primer
                                        (SEQ ID NO: 27)
5'-GGCGAGCTCTCATTTCCTGTACGTACCAGTAGA-3', ASAL mature: F primer
                                        (SEQ ID NO: 28)
5'-GGCGGATCCATGGAGGAACCTACTGACGAAC-3', ASAL mature: R primer
                                        (SEQ ID NO: 29)
5'-GGCGAGCTCTCATCTTCTGTAGGTACCAGTAGA-3', ACA mature: F primer
                                        (SEQ ID NO: 30)
5'-GGCGGATCCATGAGCGTGGCCACTGTAG-3',
and ACA mature: R primer
                                        (SEQ ID NO: 31)
5'-GGCGAGCTCTCAAGCAGCAGCAGCTGC-3',
```

All PCR amplifications were performed using Platinum PCR SuperMix High Fidelity according to the manufacturer's instructions (Invitrogen, San Diego, Calif.) with the following thermal profile: 94° C. for 2 minutes, followed by 30 cycles of 94° C. for 30 seconds, 55° C. for 30 seconds and 68° C. for 2 minutes.

In addition to the individual genes, two gene fusion cassette were also made. The first was a fusion between the mature sequences of HtA, ACA (from *Al. cepa* assagi) and ASAL (*Al. ampeloprasum*) designated as HtA::ACAas::ASALam. The second contained the mature sequence of the ACA and the ASAL gene from *Al. roseum* and designated as ACAros::ASALros. The HtA::ACAas::ASALam fusion cassette was made by PCR with the following primers:

```
HTA forward
                                        (SEQ ID NO: 32)
5'-GGATCCGAATTCGGCTTCATATGGCTCC-3', HTA reverse primer
                                        (SEQ ID NO: 33)
5'-CCCCGGGATCGCACTTCTCAAAGAACTCCT-3', ACAassagi forward primer
                                        (SEQ ID NO: 34)
5'-CCCGGGAGAAACGTATTGGTGAACAACGA-3', ACAassagi reverse primer
                                        (SEQ ID NO: 35)
5'-GGTACCTTTCCGGTATGTGCCAGTAGAC-3', ASALampeloprasum forward primer
```

-continued

```
                                     (SEQ ID NO: 36)
5'-GGTACCAGGAACCTACTGACCAACGGC-3',
and ASALampeloprasum reverse primer
                                     (SEQ ID NO: 37)
5'-GAGCTCTCACCTTCTGTAGGTACCAGTAGACC-3'.
```

Similarly, the ACAros::ASALros fusion cassette was made by PCR using the following primers:
```
ACAros forward primer
                                     (SEQ ID NO: 38)
5'-CCCGGGATGAGAAACGTATTGGTGAACAACG-3', ACAros Reverse primer
                                     (SEQ ID NO: 39)
5'-GGTACCTTTCCGGTATGTGCCAGTAGAC-3', ASALros forward primer
                                     (SEQ ID NO: 40)
5'-GGTACCAGGAACCTACTGACCAACGGC-3',
and ASALros reverse primer
                                     (SEQ ID NO: 41)
5'-GAGCTCTCACCTTCTGTAGGTACCAGTAGACC-3'.
```

For the creation of both fusion cassettes, the Platinum PCR SuperMix High Fidelity PCR Mix kit (Invitrogen, San Diego, Calif.) was used according to the manufacturer's instructions with the following thermal profile: 94° C. for 2 minutes, followed by 30 cycles of 94° C. for 30 seconds, 55° C. for 30 seconds and 68° C. for 2 minutes.

Following the preparation of cDNAs, the promoter nos-t fusion pBINplus vectors described above were purified from the DH-5a strain of *Escherichia coli*, and various combinations of the single genes cDNAs (e.g. HtA native, ACA short, MpNPR1, etc.) and the mature gene fusion cassettes (i.e HtA::ACAas::ASALam and ACAros::ASALros) were inserted between and promoter and nopaline synthase terminator (nos-t) using restriction enzyme digestion and ligation according to standard practice. Following ligation, the vectors were transformed back into the DH-5a strain of *Escherichia coli*, using the pGEMTeasy kit (Promega, Madison, USA) as per manufacturer's instructions to await transformation into *agrobacterium* strain EHA105 for plant transformation.

TABLE 1

Constructs

| Construct Name | Promoter | Cassette contents | Host source of expressed genes |
|---|---|---|---|
| JM202 | CaMV35S | 35S::35S::nos-t | |
| JM220 | CaMV35S | 35S::35S::HtA native::nos-t | Hirsutella |
| JM204 | CaMV35S | 35S::35S::HtA short::nos-t | Hirsutella |
| JM275 | CaMV35S | 35S::35S::ACA native::nos-t | Allium cepa var. aggregatum |
| JM276 | CaMV35S | 35S::35S::ACA native::nos-t | Allium tuberosum |
| JM277 | CaMV35S | 35S::35S::ACA short::nos-t | Allium cepa var. aggregatum |
| JM278 | CaMV35S | 35S::35S::ACA short::nos-t | Allium cepa var. aggregatum. |
| JM273 | CaMV35S | 35S::35S::ASAL native::nos-t | Allium roseum |
| JM272 | CaMV35S | 35S::35S::ASAL native::nos-t | Allium ampeloprasum |
| JM274 | CaMV35S | 35S::35S::ASAL short::nos-t | Allium roseum |

TABLE 1-continued

Constructs

| Construct Name | Promoter | Cassette contents | Host source of expressed genes |
|---|---|---|---|
| JM282 | CaMV35S | 35S::35S::HtA short::ACA short::ASAL short::nos-t | Hirsutella, Allium cepa var. aggregatum, Allium tuberosum |
| JM283 | CaMV35S | 35S::35S::ACA short::ASAL short::nos-t | Allium cepa var. aggregatum., Allium roseum |
| JM210 | CaMV35S | 35S::35S::GUS::nos-t | |
| JM206 | Shpx6b | Shpx6b::nos-t | |
| JM221 | Shpx6b | Shpx6b::HtA short::nos-t | Hirsutella |
| JM264 | Shpx6b | Shpx6b::HtA short::ACA short::ASAL short::nos-t | Hirsutella, Allium cepa var. aggregatum, Allium tuberosum |
| JM285 | Shpx6b | Shpx6b::ACA short::ASAL short::nos-t | Allium tuberosum, Allium roseum |

TABLE 2

Additional Constructs

| Construct Name | Promoter | Cassette contents | Host source of expressed genes |
|---|---|---|---|
| EK101 | Sus1 | Sus1::HtA short::ACA short::ASAL short::nos-t | Prunus domestica, Hirsutella, Allium cepa var. aggregatum, Allium tuberosum |
| EK102 | Sus1 | Sus1::MpNPR1::nos-t | Prunus domestica, Malus x domestica |
| EK103 | Sus1 | Sus1::CsNPR1::nos-t | Prunus domestica, Citrus sinensis |
| EK104 | CsSUS1 | CsSUS1::HtA short::ACA short::ASAL short::nos-t | Citrus sinensis, Hirsutella, Allium cepa var. aggregatum, Allium tuberosum |
| EK105 | CsSUS1 | CsSUS1::MpNPR1::nos-t | Citrus sinensis, Malus x domestica |
| EK106 | CsSUS1 | CsSUS1::CsNPR1::nos-t | Citrus sinensis |

Example 2

Transgenic tomato plants were obtained by *Agrobacterium tumefaciens*-mediated transformation according to standard methods using the plant expression constructs described in Example 1.

Transgenic plants were bioassayed for attractiveness to the tomato psyllid, *B. cockerelli*, by placing them in small chambers containing transgenic and control non-transformed leaves. Those plants on whose leaves the psyllids did not remain were identified as less attractive to psyllids, and therefore less likely to be probed by the psyllids' feeding proboscises. A typical assay involves preparing a chamber containing control and transgenic tomato leaves and introducing approximately 5 psyllids into the chamber. Eighteen to twenty-four hours after setting up the assay, psyllid location is monitored by counting the number of psyllids on a transgenic leaf compared with the number on control leaves. Transgenic plant lines are taken as useful when 0 or 1 psyllid is found on transgenic leaves, with a higher number of psyllids found on control leaves.

In some, but not all, experiments, transgenic leaves were less attractive to psyllids than control leaves. Table 3 below shows select results of transgenic lines identified as less attractive to psyllids.

TABLE 3

| Construct | Promoter | Gene | Source | # Transgenic lines | # non-attractive lines | % non-attractive lines |
|---|---|---|---|---|---|---|
| 204 | 35S | Hta short | Hirsutella | 12 | 4 | 33 |
| 221 | Shpx6b | Hta short | Hirsutella | 8 | 4 | 50 |
| Total | | Hta short | Hirsutella | 20 | 8 | 40 |
| 272 | 35S | ASALA long | Allium ampeloprasum | 27 | 3 | 11 |
| 274 | 35S | ASALR short | Allium roseum | 20 | 3 | 15 |
| 277 | 35S | ACA short | Allium cepa aggregatum | 86 | 14 | 16 |
| 278 | 35S | ACT short | Allium tuberosum | 49 | 7 | 14 |
| 282 | 35S | Hta-ACA-ASALR | Hirsutella, Allium cepa aggregatum, and Allium roseum | 34 | 5 | 15 |
| 283 | 35S | ACA-ASALR | Allium cepa aggregatum and Allium roseum | 35 | 9 | 26 |
| NPR1 | 35S | MpNPR1 | Apple | 22 | 5 | 23 |

The gene Hta from *Hirsutella* fungus was most effective in tomato in deterring psyllid feeding. The stacked construct with two *Allium* agglutinin (ACA-ASALR) genes was effective in deterring psyllid feeding as well.

Example 3—Prevention of Citrus Greening

Citrus greening (Huanglongbing, HLB) is caused by a phloem-limited walled bacterium, *Candidatus Liberibacter asiaticus*. HLB is vectored by the Asian citrus psyllid (*Diaphorina citri*). Bioassays of tomato plants that have been transformed with several genes from the *Hirsutella* fungus that colonizes insects and from *Allium* (the onion family) species evidenced that incorporation of these genes in transgenic lines inhibited feeding by psyllid insects. Constructs rendering tomato plants "non-attractive" to the tomato psyllid are then tested in orange plants to determine whether such constructs render orange plants non-attractive to the Asian citrus psyllid, and therefore would be likely to interfere with transmission of the bacterium causing HLB.

Transgenic 'Hamlin' sweet orange (*Citrus sinensis* (L.) Osbeck) plants are obtained by *Agrobacterium tumefaciens*-mediated transformation according to standard methods using the plant expression constructs described in Example 1. Constructs JM204, JM277, and JM282 are especially useful in the invention.

In particular, transgenic Hamlin plants have been generated using JM277 (ACA short) and JM282 (Hta-ACA-ASALR) constructs.

Transgenic Hamlin plants are identified and bioassayed for non-attractiveness to the Asian citrus psyllid by placing psyllids in small chambers containing transgenic and control non-transformed leaves (e.g., juvenile leaves) as is described in Example 2. Those plants on whose leaves psyllids do not remain are identified as less attractive to psyllids as is described in Example 2, and therefore less likely to be probed by the psyllids' feeding proboscises. Such non-attractive transgenic citrus plants are taken as being useful in the invention.

Example 4—Prevention of Psyllid Yellows and Zebra Chip Disease in Potatoes

Zebra chip disease in potatoes is thought to be caused by *Liberibacter solanacearum*, vectored by *B. cockerelli*, the potato/tomato psyllid. Psyllid yellows is a potato disease that is thought to be caused by a toxin produced by the nymph stage of the potato/tomato psyllid. Bioassays of tomato plants that have been transformed with several genes from the *Hirsutella* fungus that colonizes insects and from *Allium* (the onion family) species evidenced that incorporation of these genes inhibited feeding by psyllid insects. It is hypothesized that the "non-attractiveness" of these transformed tomato plants to *B. cockerelli* suggest that transforming the same genes in potato plants will reduce the feeding of the psyllid and therefore interfere with transmission of *Liberibacter solanacearum*, the cause of zebra chip disease, and the toxin that induces psyllid yellows.

Transgenic potato (*Solanum tuberosum* L.) plants are obtained by *Agrobacterium tumefaciens*-mediated transformation according to standard methods using the plant expression constructs described in Example 1. Constructs JM204, JM277, and JM282 are predicted to be especially useful in the invention.

Transgenic potato plants are identified and bioassayed for non-attractiveness to *B. cockerelli* by placing the insects in small chambers containing transgenic and control non-transformed leaves as described in Example 2. Those plants on whose leaves the psyllids do not remain are identified as less attractive to psyllids as is described in Example 2, and therefore less likely to be probed by the psyllids' feeding proboscises and to be the recipients of bacteria and toxins. Such non-attractive transgenic plants are taken as being useful in the invention.

As various modifications could be made in the constructions and methods herein described and illustrated without departing from the scope of the invention, it is intended that all matter contained in the foregoing description shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A plant comprising at least a single transgene encoding a heterologous polypeptide conferring on said plant expressing said polypeptide resistance to a hemipteroid sap-sucking insect;
   wherein said transgene comprises a lectin gene having at least 95% identity to SEQ ID NO:5; and wherein said heterologous polypeptide has at least 95% identity to SEQ ID NO:6.

2. The plant of claim 1, wherein said transgene is expressed in a plant component.

3. The plant of claim 2, wherein said plant component is a leaf.

4. The plant of claim 1, wherein said insect is a psyllid.

5. The plant of claim 4, wherein said psyllid is the Asian citrus psyllid, the African citrus psyllid, or the American citrus psyllid.

6. The plant of claim 1, wherein said plant is a citrus plant or a solanaceous plant.

7. The plant of claim 1, wherein the transgene encoding said heterologous polypeptide is stacked with a transgene encoding a ribotoxin polypeptide or a polypeptide expressed by a regulatory gene involved in basal plant resistance.

8. A product derived from the plant of claim 1, wherein said product comprises a detectable amount of said transgene or said polypeptide or an herbicide resistance gene.

9. The product of claim 8, wherein said product is a citrus product, a potato product, or a tomato product.

10. A plant of claim 1, further comprising an herbicide resistance gene conferring resistance to an herbicide.

11. A method of generating a transgenic plant resistant to a psyllid, comprising introducing into a plant cell a polynucleotide having at least 95% identity to SEQ ID NO:5, wherein said polynucleotide is expressed under the control of a heterologous promoter; and regenerating from said plant cell a transgenic plant expressing an insect inhibitory amount of a polypeptide encoded by said polynucleotide, wherein said polypeptide has at least 95% identity to SEQ ID NO:6; thereby rendering said transgenic plant resistant to said psyllid.

12. The plant of claim 1, wherein the transgene comprises the nucleotide sequence of SEQ ID NO: 5.

13. The plant of claim 1, wherein the heterologous polypeptide comprises the amino acid sequence of SEQ ID NO: 6.

14. The method of claim 11, wherein the transgene comprises the nucleotide sequence of SEQ ID NO: 5.

15. The plant of claim 11, wherein the polypeptide comprises the amino acid sequence of SEQ ID NO: 6.

* * * * *

SEQUENCE LISTING

```
<160> NUMBER OF SEQ ID NOS: 41

<210> SEQ ID NO 1
<211> LENGTH: 495
<212> TYPE: DNA
<213> ORGANISM: Hirsutella thompsonii

<400> SEQUENCE: 1
atgaaggcct ttactgccat tctcgccagc gcggccttgt tcgccaccgg cctcgcggct      60
cccgcctcag aagccacctc ggtgaacagc ctggaagagc gcgctcccat cgtcacctgc     120
cggcccaagc tcgacgggcg ggagaagccg ttcaaggtag acgtggcgac ggcgcaggca     180
caggcgcgca aggcgggcct gacgacgggc aagagcggcg accctcaccg gtacttcgcc     240
ggcgaccaca tccgctgggg cgtcaacaac tgcgacaagg cggacgcgat cctgtgggag     300
tacccgatct actgggtcgg caagaacgcc gagtgggcca aggacgtcaa gacgtcgcag     360
caaaagggag ggccgacgcc gatccgcgtc gtctacgcca acagcagggg cgccgtgcag     420
tactgcggcg tcatgacgca cagcaaggtc gacaagaata accagggcaa ggagttcttt     480
gagaagtgcg attag                                                      495

<210> SEQ ID NO 2
<211> LENGTH: 164
<212> TYPE: PRT
<213> ORGANISM: Hirsutella thompsonii

<400> SEQUENCE: 2

Met Lys Ala Phe Thr Ala Ile Leu Ala Ser Ala Ala Leu Phe Ala Thr
1               5                   10                  15

Gly Leu Ala Ala Pro Ala Ser Glu Ala Thr Ser Val Asn Ser Leu Glu
            20                  25                  30

Glu Arg Ala Pro Ile Val Thr Cys Arg Pro Lys Leu Asp Gly Arg Glu
        35                  40                  45

Lys Pro Phe Lys Val Asp Val Ala Thr Ala Gln Ala Gln Ala Arg Lys
    50                  55                  60

Ala Gly Leu Thr Thr Gly Lys Ser Gly Asp Pro His Arg Tyr Phe Ala
65                  70                  75                  80

Gly Asp His Ile Arg Trp Gly Val Asn Asn Cys Asp Lys Ala Asp Ala
                85                  90                  95

Ile Leu Trp Glu Tyr Pro Ile Tyr Trp Val Gly Lys Asn Ala Glu Trp
            100                 105                 110

Ala Lys Asp Val Lys Thr Ser Gln Gln Lys Gly Gly Pro Thr Pro Ile
        115                 120                 125

Arg Val Val Tyr Ala Asn Ser Arg Gly Ala Val Gln Tyr Cys Gly Val
    130                 135                 140

Met Thr His Ser Lys Val Asp Lys Asn Asn Gln Gly Lys Glu Phe Phe
145                 150                 155                 160

Glu Lys Cys Asp

<210> SEQ ID NO 3
<211> LENGTH: 396
<212> TYPE: DNA
<213> ORGANISM: Hirsutella thompsonii
```

<400> SEQUENCE: 3

```
atggctccca tcgtcacctg ccggcccaag ctcgacgggc gggagaagcc gttcaaggta     60
gacgtggcga cggcgcaggc acaggcgcgc aaggcgggcc tgacgacggg caagagcggc    120
gaccctcacc ggtacttcgc cggcgaccac atccgctggg gcgtcaacaa ctgcgacaag    180
gcggacgcga tcctgtggga gtacccgatc tactgggtcg gcaagaacgc cgagtgggcc    240
aaggacgtca agacgtcgca gcaaaaggga gggccgacgc cgatccgcgt cgtctacgcc    300
aacagcaggg gcgccgtgca gtactgcggc gtcatgacgc acagcaaggt cgacaagaat    360
aaccagggca aggagttctt tgagaagtgc gattag                              396
```

<210> SEQ ID NO 4
<211> LENGTH: 131
<212> TYPE: PRT
<213> ORGANISM: Hirsutella thompsonii

<400> SEQUENCE: 4

```
Met Ala Pro Ile Val Thr Cys Arg Pro Lys Leu Asp Gly Arg Glu Lys
1               5                   10                  15

Pro Phe Lys Val Asp Val Ala Thr Ala Gln Ala Gln Ala Arg Lys Ala
            20                  25                  30

Gly Leu Thr Thr Gly Lys Ser Gly Asp Pro His Arg Tyr Phe Ala Gly
        35                  40                  45

Asp His Ile Arg Trp Gly Val Asn Asn Cys Asp Lys Ala Asp Ala Ile
    50                  55                  60

Leu Trp Glu Tyr Pro Ile Tyr Trp Val Gly Lys Asn Ala Glu Trp Ala
65                  70                  75                  80

Lys Asp Val Lys Thr Ser Gln Gln Lys Gly Gly Pro Thr Pro Ile Arg
                85                  90                  95

Val Val Tyr Ala Asn Ser Arg Gly Ala Val Gln Tyr Cys Gly Val Met
            100                 105                 110

Thr His Ser Lys Val Asp Lys Asn Asn Gln Gly Lys Glu Phe Phe Glu
        115                 120                 125

Lys Cys Asp
    130
```

<210> SEQ ID NO 5
<211> LENGTH: 513
<212> TYPE: DNA
<213> ORGANISM: Allium ampeloprasum

<400> SEQUENCE: 5

```
atgagcgtgg ccactgtagc caccatccta accattttgg catctacatg catggccaga     60
aacgtattgg tgaacaacga aggactgtac gcaggccaat ccctagtcga ggaacagtac    120
acttttataa tgcaggatga ctgcaacctt gtactgtatg aatacagcac ccccatctgg    180
gcctcaaaca caggcatcac cggtaaaaat gggtgcaggg ccgtgatgca gcctgatggc    240
aactttgtcg tctacgatgt taaggggcgt gccgtctggg ccagtaacag cagaagaggg    300
aacgggaact atatcctggt gcttcagaag gacagaaacg ttgttattta cggatctgat    360
atttggtcta ctggcacata ccggaaaaaa gtgggtggaa ctgttgttat ggctatgagt    420
ggtacggtcg atggaggctc cgcgattgga ccggtaacag tgaatcagaa tgtcactgcc    480
gtccgaaagg ttgcagcagc tgctgctgct tga                                 513
```

<210> SEQ ID NO 6

```
<211> LENGTH: 170
<212> TYPE: PRT
<213> ORGANISM: Allium ampeloprasum

<400> SEQUENCE: 6

Met Ser Val Ala Thr Val Ala Thr Ile Leu Thr Ile Leu Ala Ser Thr
1               5                   10                  15

Cys Met Ala Arg Asn Val Leu Val Asn Asn Glu Gly Leu Tyr Ala Gly
            20                  25                  30

Gln Ser Leu Val Glu Glu Gln Tyr Thr Phe Ile Met Gln Asp Asp Cys
        35                  40                  45

Asn Leu Val Leu Tyr Glu Tyr Ser Thr Pro Ile Trp Ala Ser Asn Thr
    50                  55                  60

Gly Ile Thr Gly Lys Asn Gly Cys Arg Ala Val Met Gln Pro Asp Gly
65                  70                  75                  80

Asn Phe Val Val Tyr Asp Val Lys Gly Arg Ala Val Trp Ala Ser Asn
                85                  90                  95

Ser Arg Arg Gly Asn Gly Asn Tyr Ile Leu Val Leu Gln Lys Asp Arg
            100                 105                 110

Asn Val Val Ile Tyr Gly Ser Asp Ile Trp Ser Thr Gly Thr Tyr Arg
        115                 120                 125

Lys Lys Val Gly Gly Thr Val Val Met Ala Met Ser Gly Thr Val Asp
    130                 135                 140

Gly Gly Ser Ala Ile Gly Pro Val Thr Val Asn Gln Asn Val Thr Ala
145                 150                 155                 160

Val Arg Lys Val Ala Ala Ala Ala Ala
                165                 170

<210> SEQ ID NO 7
<211> LENGTH: 513
<212> TYPE: DNA
<213> ORGANISM: Allium roseum

<400> SEQUENCE: 7
atgagcgtgg ccactgtagc caccatccta accattttgg catctacatg catggccaga      60
aacgtattgg tgaacaacga aggactgtac gcaggccaat ccctagtcga ggaacagtac     120
actttttataa tgcaggatga ctgcaacctt gtactgtatg aatacagcac ccccatctgg    180
gcctcaaaca cgggcatcac cggtaaaaat gggtgcaggg ccgtgatgca gcctgatggc    240
aactttgtcg tctacgatgt taaggggcgt gccgtctggg ccagtaacag cagaagaggg    300
aacgggaact atatcctggt gcttcagaag gacagaaacg ttgttattta cggatctgat    360
atttggtcta ctggcacata ccggaaaaaa gtgggtggaa ctgttgttat ggctatgaat    420
ggtacggtcg atggaggctc cgcgattgga ccggtaacag tgaatcagaa tgtcactgcc   480
gtccgaaagg ttgcagcagc tgctgctgct tga                                  513

<210> SEQ ID NO 8
<211> LENGTH: 170
<212> TYPE: PRT
<213> ORGANISM: Allium roseum

<400> SEQUENCE: 8

Met Ser Val Ala Thr Val Ala Thr Ile Leu Thr Ile Leu Ala Ser Thr
1               5                   10                  15

Cys Met Ala Arg Asn Val Leu Val Asn Asn Glu Gly Leu Tyr Ala Gly
            20                  25                  30
```

Gln Ser Leu Val Glu Glu Gln Tyr Thr Phe Ile Met Gln Asp Asp Cys
            35                  40                  45

Asn Leu Val Leu Tyr Glu Tyr Ser Thr Pro Ile Trp Ala Ser Asn Thr
 50                  55                  60

Gly Ile Thr Gly Lys Asn Gly Cys Arg Ala Val Met Gln Pro Asp Gly
 65                  70                  75                  80

Asn Phe Val Val Tyr Asp Val Lys Gly Arg Ala Val Trp Ala Ser Asn
                 85                  90                  95

Ser Arg Arg Gly Asn Gly Asn Tyr Ile Leu Val Leu Gln Lys Asp Arg
            100                 105                 110

Asn Val Val Ile Tyr Gly Ser Asp Ile Trp Ser Thr Gly Thr Tyr Arg
            115                 120                 125

Lys Lys Val Gly Gly Thr Val Val Met Ala Met Asn Gly Thr Val Asp
            130                 135                 140

Gly Gly Ser Ala Ile Gly Pro Val Thr Val Asn Gln Asn Val Thr Ala
145                 150                 155                 160

Val Arg Lys Val Ala Ala Ala Ala Ala
                165                 170

<210> SEQ ID NO 9
<211> LENGTH: 336
<212> TYPE: DNA
<213> ORGANISM: Allium roseum

<400> SEQUENCE: 9
atgaggaacc tactgacgaa cggcgaagga ctgtatgcag ggcaatccct agatgtagaa      60
cagtacaagt ttataatgca ggatgactgc aacctcgtat tgtacgaata cagcaccccc     120
atctgggcct caaacaccgg tgtcactggc aaaaacgggt gcagggctgt catgcaaaag     180
gacggcaact ttgtggtcta cgatgttaac gggcgtcccg tctgggccag taacagtgta     240
agagggaatg gaactatat cctggtgctt caggaggaca ggaacgttgt catttacggc     300
tctgatattt ggtctactgg tacctacaga agatga                              336

<210> SEQ ID NO 10
<211> LENGTH: 112
<212> TYPE: PRT
<213> ORGANISM: Allium roseum

<400> SEQUENCE: 10

Met Leu Arg Asn Leu Leu Thr Asn Gly Glu Gly Leu Tyr Ala Gly Gln
  1               5                  10                  15

Ser Leu Asp Val Glu Gln Tyr Lys Phe Ile Met Gln Asp Asp Cys Asn
             20                  25                  30

Leu Val Leu Tyr Glu Tyr Ser Thr Pro Ile Trp Ala Ser Asn Thr Gly
         35                  40                  45

Val Thr Gly Lys Asn Gly Cys Arg Ala Val Met Gln Lys Asp Gly Asn
 50                  55                  60

Phe Val Val Tyr Asp Val Asn Gly Arg Pro Val Trp Ala Ser Asn Ser
 65                  70                  75                  80

Val Arg Gly Asn Gly Asn Tyr Ile Leu Val Leu Gln Glu Asp Arg Asn
             85                  90                  95

Val Val Ile Tyr Gly Ser Asp Ile Trp Ser Thr Gly Thr Tyr Arg Arg
            100                 105                 110

<210> SEQ ID NO 11
<211> LENGTH: 513

<212> TYPE: DNA
<213> ORGANISM: Allium cepa

<400> SEQUENCE: 11

```
atgagcgtgg ccactgtagc caccatccta accattttgg catctacatg catggccaga      60
aacgtattgg tgaacaacga aggactgtac gcaggccaat ccctagtcga ggaacagtac     120
acttttataa tgcaggatga ctgcaacctt gtactgtatg aatacagcac ccccatctgg     180
gcctcaaaca cgggcatcac cggtaaaaat gggtgcaggg ccgtgatgca gcctgatggc     240
aactttgtcg tctacgatgt taaggggcgt gccgtctggg ccagtaacag cagaagaggg     300
aacgggaact atatcctggt gcttcagaag gacagaaacg ttgttattta cggatctgat     360
atttggtcta ctggcacata ccggaaaaaa gtgggtggaa ctgttgttat ggctatgaat     420
ggtacggtcg atggaggctc cgcgattgga ccggtaacag tgaatcagaa tgtcactgcc     480
gtccgaaagg ttgcagcagc tgctgctgct tga                                  513
```

<210> SEQ ID NO 12
<211> LENGTH: 170
<212> TYPE: PRT
<213> ORGANISM: Allium cepa

<400> SEQUENCE: 12

```
Met Ser Val Ala Thr Val Ala Thr Ile Leu Thr Ile Leu Ala Ser Thr
1               5                   10                  15

Cys Met Ala Arg Asn Val Leu Val Asn Asn Glu Gly Leu Tyr Ala Gly
            20                  25                  30

Gln Ser Leu Val Glu Glu Gln Tyr Thr Phe Ile Met Gln Asp Asp Cys
        35                  40                  45

Asn Leu Val Leu Tyr Glu Tyr Ser Thr Pro Ile Trp Ala Ser Asn Thr
    50                  55                  60

Gly Ile Thr Gly Lys Asn Gly Cys Arg Ala Val Met Gln Pro Asp Gly
65                  70                  75                  80

Asn Phe Val Val Tyr Asp Val Lys Gly Arg Ala Val Trp Ala Ser Asn
                85                  90                  95

Ser Arg Arg Gly Asn Gly Asn Tyr Ile Leu Val Leu Gln Lys Asp Arg
            100                 105                 110

Asn Val Val Ile Tyr Gly Ser Asp Ile Trp Ser Thr Gly Thr Tyr Arg
        115                 120                 125

Lys Lys Val Gly Gly Thr Val Val Met Ala Met Asn Gly Thr Val Asp
    130                 135                 140

Gly Gly Ser Ala Ile Gly Pro Val Thr Val Asn Gln Asn Val Thr Ala
145                 150                 155                 160

Val Arg Lys Val Ala Ala Ala Ala Ala
                165                 170
```

<210> SEQ ID NO 13
<211> LENGTH: 336
<212> TYPE: DNA
<213> ORGANISM: Allium cepa

<400> SEQUENCE: 13

```
atgagaaacg tattggtgaa caacgaagga ctgtacgcag ccaatccct agtcgaggaa       60
cagtacactt ttataatgca ggatgactgc aaccttgtac tgtatgaata cagcaccccc     120
atctgggcct caaacacggg catcaccggt aaaaatgggt gcaggccgt gatgcagcct      180
gatggcaact tgtcgtctac gatgttaag gggcgtgccg tctgggccag taacagcaga      240
```

```
agagggaacg ggaactatat cctggtgctt cagaaggaca gaaacgttgt tatttacgga    300
tctgatattt ggtctactgg tacgtacagg aaatga                              336
```

<210> SEQ ID NO 14
<211> LENGTH: 111
<212> TYPE: PRT
<213> ORGANISM: Allium cepa

<400> SEQUENCE: 14

```
Met Arg Asn Val Leu Val Asn Asn Glu Gly Leu Tyr Ala Gly Gln Ser
1               5                   10                  15

Leu Val Glu Glu Gln Tyr Thr Phe Ile Met Gln Asp Asp Cys Asn Leu
            20                  25                  30

Val Leu Tyr Glu Tyr Ser Thr Pro Ile Trp Ala Ser Asn Thr Gly Ile
        35                  40                  45

Thr Gly Lys Asn Gly Cys Arg Ala Val Met Gln Pro Asp Gly Asn Phe
    50                  55                  60

Val Val Tyr Asp Val Lys Gly Arg Ala Val Trp Ala Ser Asn Ser Arg
65                  70                  75                  80

Arg Gly Asn Gly Asn Tyr Ile Leu Val Leu Gln Lys Asp Arg Asn Val
                85                  90                  95

Val Ile Tyr Gly Ser Asp Ile Trp Ser Thr Gly Thr Tyr Arg Lys
            100                 105                 110
```

<210> SEQ ID NO 15
<211> LENGTH: 513
<212> TYPE: DNA
<213> ORGANISM: Allium tuberosum

<400> SEQUENCE: 15

```
atgagcgtgg ccactgtagc caccatccta accattttgg catctacatg catggccaga    60
aacgtattgg tgaacaacga aggactgtac gcaggccaat ccctagtcga ggaacagtac    120
acttttataa tgcaggatga ctgcaacctt gtactgtatg aatacagcac ccccatctgg    180
gcctcaaaca caggcatcac cggtaaaaat gggtgcaggg ccgtgatgca gcctgatggc    240
aactttgtcg tctacgatgt taaggggcgt gccgtctggg ccagtaacag cagaagaggg    300
aacgggaact atatcctggt gcttcagaag gacagaaacg ttgttattta cggatctgat    360
atttggtcta ctggcacata ccggaaaaaa gtgggtggaa ctgttgttat ggctatgagt    420
ggtacggtcg atggaggctc cgcgattgga ccggtaacag tgaatcagaa tgtcactgcc    480
gtccgaaagg ttgcagcagc tgctgctgct tga                                 513
```

<210> SEQ ID NO 16
<211> LENGTH: 170
<212> TYPE: PRT
<213> ORGANISM: Allium tuberosum

<400> SEQUENCE: 16

```
Met Ser Val Ala Thr Val Ala Thr Ile Leu Thr Ile Leu Ala Ser Thr
1               5                   10                  15

Cys Met Ala Arg Asn Val Leu Val Asn Asn Glu Gly Leu Tyr Ala Gly
            20                  25                  30

Gln Ser Leu Val Glu Glu Gln Tyr Thr Phe Ile Met Gln Asp Asp Cys
        35                  40                  45

Asn Leu Val Leu Tyr Glu Tyr Ser Thr Pro Ile Trp Ala Ser Asn Thr
    50                  55                  60
```

Gly Ile Thr Gly Lys Asn Gly Cys Arg Ala Val Met Gln Pro Asp Gly
65                  70                  75                  80

Asn Phe Val Val Tyr Asp Val Lys Gly Arg Ala Val Trp Ala Ser Asn
                85                  90                  95

Ser Arg Arg Gly Asn Gly Asn Tyr Ile Leu Val Leu Gln Lys Asp Arg
            100                 105                 110

Asn Val Val Ile Tyr Gly Ser Asp Ile Trp Ser Thr Gly Thr Tyr Arg
        115                 120                 125

Lys Lys Val Gly Gly Thr Val Met Ala Met Ser Gly Thr Val Asp
    130                 135                 140

Gly Gly Ser Ala Ile Gly Pro Val Thr Val Asn Gln Asn Val Thr Ala
145                 150                 155                 160

Val Arg Lys Val Ala Ala Ala Ala Ala
                165                 170

<210> SEQ ID NO 17
<211> LENGTH: 336
<212> TYPE: DNA
<213> ORGANISM: Allium tuberosum

<400> SEQUENCE: 17
atgagaaacg tattggtgaa caacgaagga ctgtacgcag gccaatccct agtcgaggaa      60
cagtacactt ttataatgca ggatgactgc aaccttgtac tgtatgaata cagcaccccc     120
atctgggcct caaacacagg catcaccggt aaaaatgggt gcagggccgt gatgcagcct     180
gatggcaact tgtcgtcta cgatgttaag gggcgtgccg tctgggccag taacagcaga     240
agagggaacg ggaactatat cctggtgctt cagaaggaca gaaacgttgt tatttacgga     300
tctgatattt ggtctactgg tacgtacagg aaatga                              336

<210> SEQ ID NO 18
<211> LENGTH: 111
<212> TYPE: PRT
<213> ORGANISM: Allium tuberosum

<400> SEQUENCE: 18

Met Arg Asn Val Leu Val Asn Asn Glu Gly Leu Tyr Ala Gly Gln Ser
1               5                   10                  15

Leu Val Glu Glu Gln Tyr Thr Phe Ile Met Gln Asp Asp Cys Asn Leu
            20                  25                  30

Val Leu Tyr Glu Tyr Ser Thr Pro Ile Trp Ala Ser Asn Thr Gly Ile
        35                  40                  45

Thr Gly Lys Asn Gly Cys Arg Ala Val Met Gln Pro Asp Gly Asn Phe
    50                  55                  60

Val Val Tyr Asp Val Lys Gly Arg Ala Val Trp Ala Ser Asn Ser Arg
65                  70                  75                  80

Arg Gly Asn Gly Asn Tyr Ile Leu Val Leu Gln Lys Asp Arg Asn Val
                85                  90                  95

Val Ile Tyr Gly Ser Asp Ile Trp Ser Thr Gly Thr Tyr Arg Lys
            100                 105                 110

<210> SEQ ID NO 19
<211> LENGTH: 1761
<212> TYPE: DNA
<213> ORGANISM: Malus domestica

<400> SEQUENCE: 19

```
atggctcatt cagccgaacc atcatcctct ctgagcttta cttcatcacc ccatttatca      60
aatggttcaa taagccacaa cttatcgtgt tctggctccg aatcggtgcc aagtcttgaa     120
gtcatcagtt tgtccaagct tagctctagt ttggagcagt tgttgattga tcctggctgt     180
gactatagtg atgctgatat cgtagttgag gggattcctg ttggtgtaca ccgatgtata     240
ttggcttcta ggagtggatt ttttcgcgag ctattcaagc gagaaaaggg gtcttctgga     300
aaggaagaca ggccaaagta ctgtatgagt gattttctgc cttatggcga tgttggatat     360
gaagccttct tggttttctt aagctatgtg tatactggaa agcttaagcc ttctcccgtg     420
gaggtgtcaa cctgcgttca caatgtatgt gcccatgacg catgtagacc tgctatcaat     480
ttcgttgtgg aattgatgta cgccgcttcc attttccaaa tgcccgatct ggtttcgata     540
ttcgagcggc gccttcttaa ttttgttggg aaagctctgt cagacaatgt tgtcccaatt     600
ctcttggttg ccttccattg tcagttgaat cagctcatcg atcagtgtgt agatagagtg     660
gcacgatcag atattgatga catctctctt gagaagggac ttcctgatga ggttgtgaag     720
aaaatcaaaa ttcttcgccg caattatcag caggattctg acccaaactt gccacctgcc     780
gatcccttgc atgaaaagag aatccgaaga atacataagg ctttggactc ggatgatgtc     840
gagcttgtga aacttctttt aacggagtct aatataacct tagatgaagc caatgctctc     900
cattatgctg cagcttactg cgatcctaag gttgtgaccg aagtgcttgc tctgggcctc     960
gctgatgtta acctccggaa ttctaggggt atacagtgc ttcacattgc tgtgatgcgc    1020
aaagagccat caattattgt attgctactg actaaggag ctcgtgcatc ggagctgaca    1080
tcagatggtc agagtgctgt tagtatttgc aggaggttga cgagaccaaa ggattaccat    1140
tcaaaaacag agcaggggca agaagcaaac aaagaccgaa tatgcatcga tgttctagag    1200
agggaaatgc ggcggaatcc aatggctgga gatgcatcta tatcttccca ataatgccc    1260
gatgatctgc acatggagtt gctgaacctg agaacagag tggcattggc ccgattgttt    1320
ttccctgcgg aagccaagct agccatggtc attgcccatg cggagacatc tgagtttgct    1380
gcgccatcat catcgaaagg atcaagtggg aatctgatgg aggtagattt aaacgagacc    1440
cccaccgtgc agaacaaaag acttcattcc aggttggaag cccttatgaa acagtccgt    1500
ttgggtagat gctacttccc tcattgctca gaagtcctgg ataagttcat cgatgacgac    1560
ctccctcatt tgttttacct cgagcctggc tcctccgacg agcagaaggt aaagaggagg    1620
cgtttcatgg agctcaagga ggaagtacaa aaagcatttg acaaggacaa ggccgagtgt    1680
aacctctccg gattgtcttc atcgtcctcc acgacatctc cggaaaaaat tggtgcaaat    1740
cagaaggtta gggaaccgtg a                                              1761
```

<210> SEQ ID NO 20
<211> LENGTH: 586
<212> TYPE: PRT
<213> ORGANISM: Malus domestica

<400> SEQUENCE: 20

```
Met Ala His Ser Ala Glu Pro Ser Ser Leu Ser Phe Thr Ser Ser
1               5                   10                  15

Pro His Leu Ser Asn Gly Ser Ile Ser His Asn Leu Ser Cys Ser Gly
            20                  25                  30

Ser Glu Ser Val Pro Ser Leu Glu Val Ile Ser Leu Ser Lys Leu Ser
        35                  40                  45

Ser Ser Leu Glu Gln Leu Leu Ile Asp Pro Gly Cys Asp Tyr Ser Asp
    50                  55                  60
```

-continued

```
Ala Asp Ile Val Val Glu Gly Ile Pro Val Gly Val His Arg Cys Ile
 65                  70                  75                  80

Leu Ala Ser Arg Ser Gly Phe Phe Arg Glu Leu Phe Lys Arg Glu Lys
                 85                  90                  95

Gly Ser Ser Gly Lys Glu Asp Arg Pro Lys Tyr Cys Met Ser Asp Phe
            100                 105                 110

Leu Pro Tyr Gly Asp Val Gly Tyr Glu Ala Phe Leu Val Phe Leu Ser
            115                 120                 125

Tyr Val Tyr Thr Gly Lys Leu Lys Pro Ser Pro Val Glu Val Ser Thr
            130                 135                 140

Cys Val His Asn Val Cys Ala His Asp Ala Cys Arg Pro Ala Ile Asn
145                 150                 155                 160

Phe Val Val Glu Leu Met Tyr Ala Ala Ser Ile Phe Gln Met Pro Asp
                165                 170                 175

Leu Val Ser Ile Phe Glu Arg Arg Leu Leu Asn Phe Val Gly Lys Ala
                180                 185                 190

Leu Ser Asp Asn Val Pro Ile Leu Leu Val Ala Phe His Cys Gln
                195                 200                 205

Leu Asn Gln Leu Ile Asp Gln Cys Val Asp Arg Val Ala Arg Ser Asp
210                 215                 220

Ile Asp Asp Ile Ser Leu Glu Lys Gly Leu Pro Asp Glu Val Val Lys
225                 230                 235                 240

Lys Ile Lys Ile Leu Arg Arg Asn Tyr Gln Gln Asp Ser Asp Pro Asn
                245                 250                 255

Leu Pro Pro Ala Asp Pro Leu His Glu Lys Arg Ile Arg Ile His
                260                 265                 270

Lys Ala Leu Asp Ser Asp Asp Val Glu Leu Val Lys Leu Leu Leu Thr
            275                 280                 285

Glu Ser Asn Ile Thr Leu Asp Glu Ala Asn Ala Leu His Tyr Ala Ala
290                 295                 300

Ala Tyr Cys Asp Pro Lys Val Val Thr Glu Val Leu Ala Leu Gly Leu
305                 310                 315                 320

Ala Asp Val Asn Leu Arg Asn Ser Arg Gly Tyr Thr Val Leu His Ile
                325                 330                 335

Ala Val Met Arg Lys Glu Pro Ser Ile Ile Val Leu Leu Leu Thr Lys
            340                 345                 350

Gly Ala Arg Ala Ser Glu Leu Thr Ser Asp Gly Gln Ser Ala Val Ser
            355                 360                 365

Ile Cys Arg Arg Leu Thr Arg Pro Lys Asp Tyr His Ser Lys Thr Glu
370                 375                 380

Gln Gly Gln Glu Ala Asn Lys Asp Arg Ile Cys Ile Asp Val Leu Glu
385                 390                 395                 400

Arg Glu Met Arg Arg Asn Pro Met Ala Gly Asp Ala Ser Ile Ser Ser
                405                 410                 415

Gln Ile Met Pro Asp Asp Leu His Met Glu Leu Leu Asn Leu Glu Asn
            420                 425                 430

Arg Val Ala Leu Ala Arg Leu Phe Phe Pro Ala Glu Ala Lys Leu Ala
            435                 440                 445

Met Val Ile Ala His Ala Glu Thr Ser Glu Phe Ala Ala Pro Ser Ser
        450                 455                 460

Ser Lys Gly Ser Ser Gly Asn Leu Met Glu Val Asp Leu Asn Glu Thr
465                 470                 475                 480
```

```
Pro Thr Val Gln Asn Lys Arg Leu His Ser Arg Leu Glu Ala Leu Met
                485                 490                 495

Lys Thr Val Arg Leu Gly Arg Cys Tyr Phe Pro His Cys Ser Glu Val
            500                 505                 510

Leu Asp Lys Phe Ile Asp Asp Leu Pro His Leu Phe Tyr Leu Glu
        515                 520                 525

Pro Gly Ser Ser Asp Glu Gln Lys Val Lys Arg Arg Phe Met Glu
    530                 535                 540

Leu Lys Glu Glu Val Gln Lys Ala Phe Asp Lys Ala Glu Cys
545                 550                 555                 560

Asn Leu Ser Gly Leu Ser Ser Ser Ser Thr Thr Ser Pro Glu Lys
                565                 570                 575

Ile Gly Ala Asn Gln Lys Val Arg Glu Pro
            580                 585

<210> SEQ ID NO 21
<211> LENGTH: 22
<212> TYPE: DNA
<213> ORGANISM: Citrus sinensis

<400> SEQUENCE: 21
tggctgtgac tatagtgatg ct                                              22

<210> SEQ ID NO 22
<211> LENGTH: 22
<212> TYPE: DNA
<213> ORGANISM: Citrus sinensis

<400> SEQUENCE: 22
ccctaacctt ctgatttgca cc                                              22

<210> SEQ ID NO 23
<211> LENGTH: 1906
<212> TYPE: DNA
<213> ORGANISM: Prunus domestica

<400> SEQUENCE: 23
tccaatgatt gctcccatta gctaatcaaa ttaatagtac attatagtat gataagattc      60
agcatattct tcaaactatc ctctcatctt tttttattat aatgtgtgta catagtaatt     120
aaaaacatta atccaaaacc caagttggat tacattaaac ccgtgaaccc aatgggctag     180
aattgtaggg tttcataggg aacaacaact gcaaagtcta aaagtaagaa gaaactctcg     240
tgaaacgggg atagcatttt ttggtctccg gggcagtaac aacatgatac ataggataac     300
ttttccgata catatgacaa cttctccaca tgtcatgttg ttattggccg gggatagcaa     360
aacagtgcta tccgcggtat aggtgagttt ttttcctaaa aagcggccaa aagtccgact     420
tctgaatcat cacccaacca gcaccttcgc cgattagacc catgcatgcc cctctttctc     480
tgcactttcc ctgaccgcca catatttatt ttttatttca caccttaatt ccatgaattt     540
ggtgccttca atgggaaaaa aaaaaaaaaa aaaaccagaa atcccaatg gattttctt      600 gttgcccaag cccgacaaaa aaaggcaaat gcttgaatat caaggcttaa aattaaacag     660
cacaaaattg attaatcctc taatttcttt ccaaaaatcc tatcatatcc cattttcaat     720
ttgtgaattt acgaaattac ccctgttttt ttgatgactt cttcggtctt cgggtaagga     780
aatgagactg ataaaatgga tataatagat ttccgaccac cctgctggat ttttttttg      840 ccactgccct tattatcgta cgctccaagt ttttttttta cttgcctatt ttggttcgcg     900
```

-continued

```
gttccacgct ataaagcgag ctcacaccat ccaccaacca cctcacttct cttcttctcg    960
tttccatagg ctttctctct ctctctgtgt tctttgtcta ggtacacctc attttctctt   1020
cccattttta ttttccttg tgttcttgtt cttcttgttg ggttatttct ttaggctata   1080
tggtctttgc tctttttttc ttttggttca tctcccaaat cacatagatc aatgccttct   1140
gaatgtaggg ttgagtttat ttgagggtat atactctgtt tttgcttttc tgcaccagta   1200
ttttgtgcgg atctctgttt ttaattttt tccgtctgct tttgtttgtt gaaagtgaaa   1260
aagctgttta tcttttttgac tggttggtct gtttcacttc aacaagcaac cagtagaaga   1320 agtgttttc tttatcttga tggtctttt cagcttctct tttggagaaa agattgattc   1380
ttgtcaacat tcgccaaatg caccattttt attttcttc ttctttgata aaaagcgttt   1440
tctctgcttt tgctaagcac ccttaattat taatattata agcctggatt tttatgatgg   1500
gcttgaagct ttttatctgt ccgccactct gcaaatcctt tatgggtgca tctaattatt   1560
acataattaa aacctggatc tttttttcat tattcttaac cactatctaa ggttgcatct   1620
ttgttcaacc gcactgctct aattaacgtt tgtatgaggt ggttggtgga tggtgtgttt   1680 ggtttgaaa aactaaagaa attagtcttc tagaataata aataatatta ataataataa   1740
tattattatt attgtaaagt cttcctgtta atgttggaat tattgacttg gtggtgatta   1800
tccatctctt tttattgcga agcttctgga taccttgtta tactcacggc ttgctttgta   1860
cttgcagttt ttgaaggttc tctgatttac caatctgcta tcaatg               1906
```

<210> SEQ ID NO 24
<211> LENGTH: 33
<212> TYPE: DNA
<213> ORGANISM: Artificial Sequence
<220> FEATURE:
<223> OTHER INFORMATION: Synthetic Primer

<400> SEQUENCE: 24
ggcggatcca tgggtcctac tacttcatct cct           33

<210> SEQ ID NO 25
<211> LENGTH: 33
<212> TYPE: DNA
<213> ORGANISM: Artificial Sequence
<220> FEATURE:
<223> OTHER INFORMATION: Synthetic Primer

<400> SEQUENCE: 25
ggcgagctct caagcagcac cggtgccaac ctt           33

<210> SEQ ID NO 26
<211> LENGTH: 32
<212> TYPE: DNA
<213> ORGANISM: Artificial Sequence
<220> FEATURE:
<223> OTHER INFORMATION: Synthetic Primer

<400> SEQUENCE: 26
ggcggatcca tgagaaacgt attggtgaac aa            32

<210> SEQ ID NO 27
<211> LENGTH: 33
<212> TYPE: DNA
<213> ORGANISM: Artificial Sequence
<220> FEATURE:
<223> OTHER INFORMATION: Synthetic Primer

<400> SEQUENCE: 27
ggcgagctct catttcctgt acgtaccagt aga     33

<210> SEQ ID NO 28
<211> LENGTH: 30
<212> TYPE: DNA
<213> ORGANISM: Artificial Sequence
<220> FEATURE:
<223> OTHER INFORMATION: Synthetic Primer

<400> SEQUENCE: 28
ggcggatcca tgaggaacct actgacgaac     30

<210> SEQ ID NO 29
<211> LENGTH: 33
<212> TYPE: DNA
<213> ORGANISM: Artificial Sequence
<220> FEATURE:
<223> OTHER INFORMATION: Synthetic Primer

<400> SEQUENCE: 29
ggcgagctct catcttctgt aggtaccagt aga     33

<210> SEQ ID NO 30
<211> LENGTH: 28
<212> TYPE: DNA
<213> ORGANISM: Artificial Sequence
<220> FEATURE:
<223> OTHER INFORMATION: Synthetic Primer

<400> SEQUENCE: 30
ggcggatcca tgagcgtggc cactgtag     28

<210> SEQ ID NO 31
<211> LENGTH: 27
<212> TYPE: DNA
<213> ORGANISM: Artificial Sequence
<220> FEATURE:
<223> OTHER INFORMATION: Synthetic Primer

<400> SEQUENCE: 31
ggcgagctct caagcagcag cagctgc     27

<210> SEQ ID NO 32
<211> LENGTH: 28
<212> TYPE: DNA
<213> ORGANISM: Artificial Sequence
<220> FEATURE:
<223> OTHER INFORMATION: Synthetic Primer

<400> SEQUENCE: 32
ggatccgaat tcggcttcat atggctcc     28

<210> SEQ ID NO 33
<211> LENGTH: 30
<212> TYPE: DNA
<213> ORGANISM: Artificial Sequence
<220> FEATURE:
<223> OTHER INFORMATION: Synthetic Primer

<400> SEQUENCE: 33
ccccgggatc gcacttctca aagaactcct     30

<210> SEQ ID NO 34
<211> LENGTH: 29
<212> TYPE: DNA

<213> ORGANISM: Artificial Sequence
<220> FEATURE:
<223> OTHER INFORMATION: Synthetic Primer

<400> SEQUENCE: 34
cccgggagaa acgtattggt gaacaacga                                    29

<210> SEQ ID NO 35
<211> LENGTH: 28
<212> TYPE: DNA
<213> ORGANISM: Artificial Sequence
<220> FEATURE:
<223> OTHER INFORMATION: Synthetic Primer

<400> SEQUENCE: 35
ggtacctttc cggtatgtgc cagtagac                                     28

<210> SEQ ID NO 36
<211> LENGTH: 27
<212> TYPE: DNA
<213> ORGANISM: Artificial Sequence
<220> FEATURE:
<223> OTHER INFORMATION: Synthetic Primer

<400> SEQUENCE: 36
ggtaccagga acctactgac caacggc                                      27

<210> SEQ ID NO 37
<211> LENGTH: 32
<212> TYPE: DNA
<213> ORGANISM: Artificial Sequence
<220> FEATURE:
<223> OTHER INFORMATION: Synthetic Primer

<400> SEQUENCE: 37
gagctctcac cttctgtagg taccagtaga cc                                32

<210> SEQ ID NO 38
<211> LENGTH: 31
<212> TYPE: DNA
<213> ORGANISM: Artificial Sequence
<220> FEATURE:
<223> OTHER INFORMATION: Synthetic Primer

<400> SEQUENCE: 38
cccgggatga gaaacgtatt ggtgaacaac g                                 31

<210> SEQ ID NO 39
<211> LENGTH: 28
<212> TYPE: DNA
<213> ORGANISM: Artificial Sequence
<220> FEATURE:
<223> OTHER INFORMATION: Synthetic Primer

<400> SEQUENCE: 39
ggtacctttc cggtatgtgc cagtagac                                     28

<210> SEQ ID NO 40
<211> LENGTH: 27
<212> TYPE: DNA
<213> ORGANISM: Artificial Sequence
<220> FEATURE:
<223> OTHER INFORMATION: Synthetic Primer

<400> SEQUENCE: 40
ggtaccagga acctactgac caacggc                                      27

```
<210> SEQ ID NO 41
<211> LENGTH: 32
<212> TYPE: DNA
<213> ORGANISM: Artificial Sequence
<220> FEATURE:
<223> OTHER INFORMATION: Synthetic Primer

<400> SEQUENCE: 41
gagctctcac cttctgtagg taccagtaga cc                                   32
```